United States Patent
Furuya et al.

(10) Patent No.: US 6,642,379 B1
(45) Date of Patent: Nov. 4, 2003

(54) BENZAMIDE DERIVATIVES, INSECTICIDES FOR AGRICULTURAL AND HORTICULTURAL USE AND USAGE THEREOF

(75) Inventors: Takashi Furuya, Izumisano (JP); Eiji Kohno, Bisai (JP); Masanori Tohnishi, Sakai (JP); Kazuyuki Sakata, Kawachinagano (JP); Masayuki Morimoto, Kawachinagano (JP); Akira Seo, Hashimoto (JP)

(73) Assignee: Nihon Nohyaku Co., Ltd., Tokyo (JP)

( * ) Notice: Subject to any disclaimer, the term of this patent is extended or adjusted under 35 U.S.C. 154(b) by 0 days.

(21) Appl. No.: 10/018,687
(22) PCT Filed: Jun. 23, 2000
(86) PCT No.: PCT/JP00/04135
§ 371 (c)(1), (2), (4) Date: Apr. 4, 2002
(87) PCT Pub. No.: WO01/00599
PCT Pub. Date: Jan. 4, 2001

(30) Foreign Application Priority Data

Jun. 25, 1999 (JP) .................... 11-179999

(51) Int. Cl.[7] ........... C07D 265/04; C07D 263/34; C07D 417/00; A61K 31/42; A61K 31/425
(52) U.S. Cl. ........... 544/88; 548/236; 548/238; 548/205; 548/254; 546/269.7; 546/271.4; 546/272.7; 514/374; 514/365; 514/381; 514/228.8; 514/340; 514/341; 514/342
(58) Field of Search ............... 514/374, 365, 514/381, 228.8, 340, 341, 342; 548/236, 238, 205, 254; 546/269.7, 271.4, 272.7; 544/88

(56) References Cited

U.S. PATENT DOCUMENTS 5,086,184 A * 2/1992 Burow, Jr. .................. 548/246
5,962,685 A    10/1999 Ueda et al.
6,107,251 A     8/2000 Ueda et al.
6,310,005 B1 * 10/2001 Assmann et al. .......... 504/223

FOREIGN PATENT DOCUMENTS

| EP | 0 609 734 | 8/1994 |
| EP | 0 776894 | 6/1997 |
| WO | WO 93/16053 | 8/1993 |
| WO | WO 94/17059 | 8/1994 |
| WO | WO 96/4278 | 2/1996 |

* cited by examiner

*Primary Examiner*—Deborah C. Lambkin
(74) *Attorney, Agent, or Firm*—Paul E. White, Jr.; Manelli Denison & Selter PLLC

(57) ABSTRACT

Benzamide derivatives represented by the general formula (I):

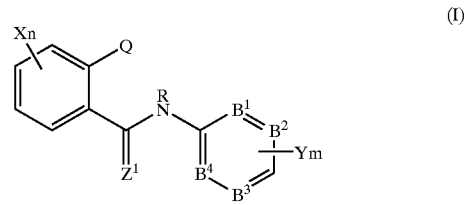

and insecticides for agricultural and horticultural use and usage thereof, wherein $Z^1$ is O or S; R is H, (substituted) alkyl, or alkoxycarbonyl; X is halogeno, cyano, nitro, $C_3$-$C_6$ (halo)cycloalkyl, (substituted) phenyl, a (substituted) heterocyclic group, or —$A^1$—$R^1$ [wherein $A^1$ is —O—, —S—, —SO—, —SO$_2$—, —C(=O)—, or —C(=NOR$_2$)— (wherein $R^2$ is H, $C_1$-$C_6$(halo)alkyl, (substituted) phenylated $C_1$-$C_4$ alkyl, or the like); and $R^1$ is halogeno, $C_3$-$C_6$ cycloalkyl, $C_3$-$C_6$ halocycloalkenyl, (substituted) phenyl, or the like]; n is 0 to 4; Y is halogeno, cyano, nitro, $C_3$-$C_6$ halocycloalkyl, (substituted) phenyl, or the like; m is 1 to 5; Q is a heterocycle such as oxazoline; and $B^1$ to $B^4$ are each CH or N.

6 Claims, No Drawings

BENZAMIDE DERIVATIVES, INSECTICIDES FOR AGRICULTURAL AND HORTICULTURAL USE AND USAGE THEREOF

This application is the national phase of international application PCT/JP00/04135 filed Jun. 23, 2000 which designated the U.S.

TECHNICAL FIELD

The present invention relates to novel benzamide derivatives and agricultural and horticultural insecticides containing, as the effective ingredient, said derivatives and method for using thereof.

BACKGROUND ART

JP-A-5-1060, JP-A(T)-507497, JP-A-6-41093 and JP-A-8-92224 disclose active insecticidal and acaricidal compounds which are analogous to the benzamide derivatives of the present invention. However, these prior arts do not disclose compounds having amide bond as the substituent on the benzene ring being bonded to the heterocyclic group.

As the result of extensive studies conducted to develop novel agricultural and horticultural chemicals, the present inventors have found novel benzamide derivatives represented by the general formula (I) which have not been disclosed in any literature and these compounds can be used for novel applications in agricultural and horticultural insecticides. Thus the present invention have been accomplished.

DISCLOSURE OF THE INVENTION

The present invention relates to the benzamide derivatives, agricultural and horticultural insecticides containing said compounds as the effective ingredient, and method for using thereof. The benzamide derivatives are represented by the general formula (I):

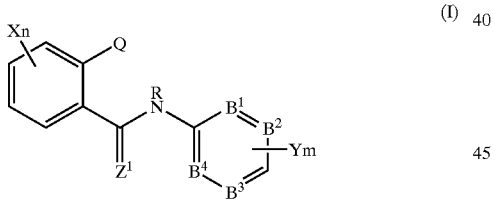

(I)

{wherein $Z^1$ is an oxygen atom or a sulfur atom; R is a hydrogen atom, an unsubstituted $C_1$–$C_6$ alkyl group, a substituted $C_1$–$C_6$ alkyl group having one or more substituents which may be the same or different and are selected from the group consisting of a halogen atom, a $C_1$–$C_6$ alkoxyl group, a $C_1$–$C_6$ alkylthio group, a $C_1$–$C_6$ alkylamino group and a di-$C_1$–$C_6$ alkylamino group whose $C_1$–$C_6$ alkyl groups may be the same or different, or a $C_1$–$C_6$ alkoxycarbonyl group;

X, which may be the same or different, are halogen atoms, cyano groups, nitro groups, $C_3$–$C_6$ cycloalkyl groups, halo-$C_3$–$C_6$ cycloalkyl groups, tri-$C_1$–$C_6$ alkylsilyl groups whose $C_1$–$C_6$ alkyl groups may be the same or different, unsubstituted phenyl groups, substituted phenyl groups having one or more substituents which may be the same or different and are selected from the group consisting of a halogen atom, a $C_1$–C alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and halo-$C_1$–$C_6$ alkylsulfonyl group, unsubstituted heterocyclic groups, substituted heterocyclic groups having one or more substitutents which may be the same or different and are selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group, or —$A^1$—$R^1$ [wherein $A^1$ is —O—, —S—, —SO—, —$SO_2$—, —C(=O)—, —C(=$NOR^2$)— (wherein $R^2$ is a hydrogen atom, a $C_1$–$C_6$ alkyl group, a halo-$C_1$–$C_6$ alkyl group, a $C_3$–$C_6$ alkenyl group, a halo-$C_1$–$C_6$ alkenyl group, a $C_3$–$C_6$ alkynyl group, a $C_3$–$C_6$ cycloalkyl group, an unsubstituted phenyl-$C_1$–$C_4$ alkyl group, or a substituted phenyl-$C_1$–$C_4$ alkyl group having one or more substitutents which may be the same or different and are selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group), a $C_1$–$C_6$ alkylene group, a halo-$C_1$–$C_6$ alkylene group, a $C_2$–$C_6$ alkenylene group, a halo-$C_2$–$C_6$ alkenylene group, a $C_2$–$C_6$ alkynylene group and a halo $C_2$–$C_6$ alkynylene group, and $R^1$ is as follows:

(1) when $A^1$ is —O—, —S—, —SO— or —$SO_2$—, then $R^1$ is a halo-$C_3$–$C_6$ cycloalkyl group, a halo-$C_3$–$C_6$ cycloalkenyl group, an unsubstituted phenyl group, a substituted phenyl group having one or more substituents which may be the same or different and are selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group, an unsubstituted hetero-cyclic group, a substituted heterocyclic group having one or more substituents which may be the same or different and are selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group, or —$A^2$—$R^3$ (wherein $A^2$ is a $C_1$–$C_6$ alkylene group, a halo-$C_1$–$C_6$ alkylene group, a $C_3$–$C_6$ alkenylene group, a halo-$C_3$–$C_6$ alkenylene group, a $C_3$–$C_6$ alkynylene group or a halo-$C_3$–$C_6$ alkynylene group; $R^3$ is a hydrogen atom, a halogen atom, a $C_3$–$C_6$ cycloalkyl group, a halo-$C_3$–$C_6$ cycloalkyl group, a $C_3$–$C_6$ alkoxycarbonyl group, an unsubstituted phenyl group, a substituted phenyl group having one or more substituents which may be the same or different and are selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo- $C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group, or —$A^3$—$R^4$ (wherein $A^3$ is —O—, —S—, —SO—, —$SO_2$— or —C(=O)—; $R^4$ is a $C_1$–$C_6$ alkyl group, a halo-$C_1$–$C_6$ alkyl group, a $C_3$–$C_6$ alkenyl group, a halo-$C_3$–$C_6$ alkenyl group, a $C_3$–$C_6$ cycloalkyl group, a halo-$C_3$–$C_6$ cycloalkyl group, an unsubstituted phenyl group, a substituted phenyl group having one or more substituents which may be the same or different and are selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group, an unsubstituted heterocyclic group, or a substituted heterocyclic group having one or more substituents which may be the same or different and are selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group)), (2) when $A^1$ is —C(=O)— or —C(=$NOR^2$)— (wherein $R^2$ is the same as defined above), then $R^1$ is a hydrogen atom, a $C_1$–$C_6$ alkyl group, a halo-$C_1$–$C_6$ alkyl group, a $C_2$–$C_6$ alkenyl group, a halo-$C_2$–$C_6$ alkenyl group, a $C_3$–$C_6$ cycloalkyl group, a halo-$C_3$–$C_6$ cycloalkyl group, a $C_1$–$C_6$ alkoxy group, a $C_1$–$C_6$ alkylthio group, a mono-$C_1$–$C_6$ alkylamino group, a di-$C_1$–$C_6$ alkylamino group whose $C_1$–$C_6$ alkyl groups may be the same or different, an unsubstituted phenyl group, a substituted phenyl group having one or more substituents which may be the same of different and are selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group, an unsubstituted phenylamino group, a substituted phenylamino group having one or more substituents which may be same or different and are selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group, an unsubstituted heterocyclic group, or a substituted heterocyclic group having one or more substituents which may be the same or different and are selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group, (3) when $A^1$ is a $C_1$–$C_6$ alkylene group, a halo-$C_1$–$C_6$ alkylene group, a $C_2$–$C_6$ alkenylene group, a halo-$C_2$–$C_6$ alkenylene group, a $C_2$–$C_6$ alkynylene group or a halo-$C_3$–$C_6$ alkynylene group, then $R^1$ is a hydrogen atom, a halogen atom, a $C_3$–$C_6$ cycloalkyl group, a halo-$C_3$–$C_6$ cycloalkyl group, a $C_1$–$C_6$ alkoxycarbonyl group, a tri-$C_1$–$C_6$ alkylsilyl group whose $C_1$–$C_6$ alkyl groups may be the same or different, an unsubstituted phenyl group, a substituted phenyl group having one or more substituents which may be the same or different and are selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group a halo-$C_1$–$C_6$ alkylthio group, a $C_1$–$C_6$ alkylsulfinyl group a halo-$C_1$–$C_6$ alkylsulfinyl group, a $C_1$–$C_6$ alkylsulfonyl group and a halo-$C_1$–$C_6$ alkylsulfonyl group, an unsubstituted heterocyclic group, a substituted heterocyclic group having one or more substituents which may be the same or different and are selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group, or —$A^4$—$R^5$ (wherein $A^4$ is —O—, —S—, —SO— or —$SO_2$—; and $R^5$ is a $C_3$–$C_6$ cycloalkyl group, a halo-$C_3$–$C_6$ cycloalkyl group, an unsubstituted phenyl group, a substituted phenyl group having one or more substituents which may be the same or different and are selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group, an unsubstituted heterocyclic group, a substituted heterocyclic group having one or more substituents which are selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group, or —$A^5$—$R^6$ (wherein $A^5$ is a $C_1$–$C_6$ alkylene group, a halo-$C_1$–$C_6$ alkylene group, a $C_2$–$C_2$ alkenylene group, a halo-$C_2$–$C_6$ alkenylene group, a $C_2$–$C_6$ alkynylene group, or a halo-$C_1$–$C_6$ alkynylene group; $R^6$ is a hydrogen atom, a halogen atom, a $C_3$–$C_6$ cycloalkyl group, a halo-$C_1$–$C_6$ cycloalkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group, an unsubstituted phenyl group, a substituted phenyl group having one or more substituents which may be the same or different and are selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group, an unsubstituted phenoxy group, a substituted phenoxy group having one or more substituents which may be the same or different and are selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group, an unsubstituted phenylthio group, a substituted phenylthio group having one or more substituents which may be the same or different and are selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group, an unsubstituted heterocyclic group, or a substituted heterocyclic group having one or more substituents which may be the same or different and are selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group))];

n is an integer of 0 to 4; further

X may be taken together with carbon atoms adjacent thereto on the phenyl ring to form a condensed ring, and said condensed ring may have one or more substituents which may be the same or different and are selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group, an unsubstituted phenyl group, a substituted phenyl group having one or more substituents which may be the same or different and are selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group, an unsubstituted heterocyclic group, and a substituted heterocyclic group having one or more substituents which may be the same or different and are selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group;

$B^1$, $B^2$, $B^3$ and $B^4$ are the same or different, and are nitrogen atoms or carbon atoms; Y, which may be the same or different, are halogen atoms, cyano groups, nitro groups, halo-$C_3$–$C_6$ cycloalkyl groups, unsubstituted phenyl groups, substituted phenyl groups having one or more substituents which may be the same or different and are selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group, unsubstituted heterocyclic groups, substituted heterocyclic groups having one or more substituents which may be same or different and are selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group, or —$A^1$—$R^1$ (wherein $A^1$ and $R^1$ are the same as defined above);

m is an integer of 1 to 5; further,

Y may be taken together with carbon atoms adjacent thereto on the aromatic ring to form a condensed ring, and said condensed ring may have one or more substituents which may be the same or different and are selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, an unsubstituted phenyl group, a substituted phenyl group having one or more substituents which may be the same or different and are selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group, an unsubstituted heterocyclic group, and a substituted heterocyclic group having one or more substituents which may be the same or different and are selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group;

Q is a heterocyclic group represented by each one of the following $Q^1$ to $Q^8$:

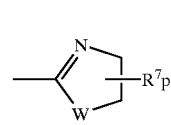

$Q^1$

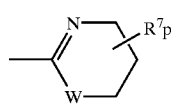

$Q^2$

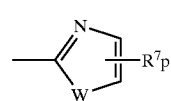

$Q^3$

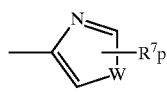
Q⁴

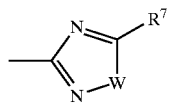
Q⁵

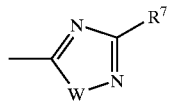
Q⁶

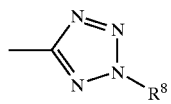
Q⁷

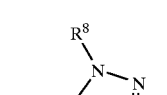
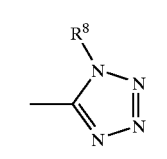
Q⁸

(wherein W is an oxygen atom, a sulfur atom or —N(R⁸)— (wherein R⁸ is a $C_1$–$C_6$ alkyl group, a halo-$C_1$–$C_6$ alkyl group, a $C_1$–$C_6$ alkoxy-$C_1$–$C_6$ alkyl group, a halo-$C_1$–$C_6$ alkoxy-$C_1$–$C_6$ alkyl group, a $C_1$–$C_6$ alkylthio-$C_1$–$C_6$ alkyl group, a halo-$C_1$–$C_6$ alkylthio-$C_1$–$C_6$ alkyl group, a $C_1$–$C_6$ alkylsulfinyl-$C_1$–$C_6$ alkyl group, a halo-$C_1$–$C_6$ alkylsulfinyl-$C_1$–$C_6$ alkyl group, a $C_1$–$C_6$ alkylsulfonyl-$C_1$–$C_6$ alkyl group, a halo-$C_1$–$C_6$ alkylsulfonyl-$C_1$–$C_6$ alkyl group, an unsubstituted phenyl group, a substituted phenyl group having one or more substituents which may be the same or different and are selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group, a $C_1$–$C_6$ alkylcarbonyl group, a halo-$C_1$–$C_6$ alkylcarbonyl group, a $C_1$–$C_6$ alkoxycarbonyl group, a $C_1$–$C_6$ alkylaminocarbonyl group, di-$C_1$–$C_6$ alkylaminocarbonyl group whose $C_1$–$C_6$ alkyl groups may be the same or different, an unsubstituted phenylcarbonyl group, a substituted phenylcarbonyl group having one or more substituents which may be the same or different and are selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group, an unsubstituted phenyl-$C_1$–$C_4$ alkoxycarbonyl group, or a substituted phenyl-$C_1$–$C_4$ alkoxycarbonyl group having one or more substituents which may be the same or different and are selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group);

$R^7$ is —($A^6$)r—$G_l$ (wherein $A^6$ is a $C_1$–$C_6$ alkylene group, a $C_3$–$C_6$ alkenylene group or $C_3$–$C_8$ alkylene group; r is an integer of 0 or 1; G, which may be the same or different, are hydrogen atoms, halogen atoms, cyano groups, nitro groups, halo-$C_1$–$C_6$ alkyl groups, $C_3$–$C_6$ cycloalkyl groups, halo-$C_3$–$C_6$ cycloalkyl groups, $C_1$–$C_6$ alkoxycarbonyl groups, di-$C_1$–$C_6$ alkoxyphosphoryl groups whose $C_1$–$C_6$ alkoxy groups may be the same or different, di-$C_1$–$C_6$ alkoxythiophosphoryl groups whose $C_1$–$C_6$ alkoxy groups may be the same or different, diphenylphosphino groups, diphenylphosphono groups, unsubstituted phenyl groups, substituted phenyl groups having one or more substituents which may be the same or different and are selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group, unsubstituted biphenyl groups, substituted biphenyl groups having one or more substituents which may be the same or different and are selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group, unsubstituted heterocyclic groups, substituted heterocyclic groups having one or more substituents which may be the same or different and are selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group, or —$A^7$—$R^9$ [wherein $A^7$ is —O—, —S—, —SO—, —$SO_2$—, —N($R^{10}$)— (wherein $R^{10}$ is a hydrogen atom, a $C_1$–$C_6$ alkylcarbonyl group, a halo-$C_1$–$C_6$ alkylcarbonyl group, a $C_1$–$C_6$ alkoxycarbonyl group, a $C_1$–$C_6$ alkylaminocarbonyl group, a di-$C_1$–$C_6$ alkylaminocarbonyl group whose $C_1$–$C_6$ alkyl groups may be the same or different, an unsubstituted phenylcarbonyl group, a substituted phenylcarbonyl group having one or more substituents which may be the same or different and are selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group, an unsubstituted phenyl-$C_1$–$C_4$ alkoxycarbonyl group, a substituted phenyl-$C_1$–$C_4$ alkoxycarbonyl group having one or more substituents which may be the same or different and are selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group, a $C_1$–$C_6$ alkylsulfonyl group or a halo-$C_1$–$C_6$ alkylsulfonyl group), —C(=O)— or —C(=NOR$^2$)—, (wherein R$^2$ is the same as defined above), and R$^9$ is as follows:

(1) when A$^7$ is —O—, —S— or —(NR$^{10}$)— (wherein R$^{10}$ is the same as defined above), then R$^9$ is a hydrogen atom, a $C_1$–$C_6$ alkyl group, a halo-$C_1$–$C_6$ alkyl group, a $C_3$–$C_6$ alkenyl group, a halo-$C_3$–$C_6$ alkenyl group, a $C_3$–$C_6$ alkynyl group, a halo-$C_3$–$C_6$ alkynyl group, a $C_3$–$C_6$ cycloalkyl group, a halo-$C_3$–$C_6$ cycloalkyl group, a $C_1$–$C_6$ alkylcarbonyl group, a halo-$C_1$–$C_6$ alkylcarbonyl group, a $C_1$–$C_6$ alkoxycarbonyl group, an unsubstituted phenyl group, a substituted phenyl group having one or more substituents which may be the same or different and are selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group, an unsubstituted phenyl-$C_1$–$C_4$ alkyl group, a substituted phenyl-$C_1$–$C_4$ alkyl group having one or more substituents in the phenyl ring which may be the same or different and are selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group, an unsubstituted heterocyclic group, or a substituted heterocyclic group having one or more substituents which may be the same or different and are selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group, (2) when A$^7$ is —SO—, —SO$_2$—, —C(=O)— or —C(=NOR$^2$)— (wherein R$^2$ is the same as defined above), then R$^9$ is a hydrogen atom, a $C_1$–$C_6$ alkyl group, a halo-$C_1$–$C_6$ alkyl group, a $C_3$–$C_6$ alkenyl group, a halo-$C_3$–$C_6$ alkenyl group, a $C_3$–$C_6$ cycloalkyl group, a halo-$C_3$–$C_6$ cycloalkyl group, a $C_3$–$C_6$ alkoxy group, a $C_1$–$C_6$ alkylthio group, a mono-$C_1$–$C_6$ alkylamino group, a di-$C_1$–$C_6$ alkylamino group whose $C_1$–$C_6$ alkyl groups may be the same or different, an unsubstituted phenyl group, a substituted phenyl group having one or more substituents which may be the same or different and are selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group, an unsubstituted phenylamino group, a substituted phenylamino group having one or more substituents which may be the same or different in the phenyl ring and are selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group, an unsubstituted heterocyclic group, or a substituted heterocyclic group having one or more substituents which may be the same or different and are selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group];

l is an integer of 1 to 4); R$^8$ is the same as defined above; and p is as follows, (1) when Q is Q$^1$, then p is an integer of 1–4; and R$^7$ may form 5–7 membered heterocyclic group by bonding together with carbon atoms adjacent thereto on the heterocyclic group, and the newly formed 5–7 membered heterocyclic group may be interrupted by 1–3 heteroatoms which may be the same or different and selected from oxygen atom, sulfur atom and nitrogen atom, additionally, R$^7$ may form 3–7 membered heterocyclic group by bonding together with the same carbon atoms being bonded thereto on the heterocyclic group, and the newly formed 3–7 membered heterocyclic group may be interrupted by 1–3 heteroatoms which may be the same or different and selected from oxygen atom, sulfur atom and nitrogen atom;

(2) when Q is Q$^2$, then p is an integer of 1–6; and R$^7$ may form 5–7 membered heterocyclic group by bonding together with carbon atoms adjacent thereto on the heterocyclic group, and the newly formed 5–7 membered heterocyclic group may be interrupted by 1–3 heteroatoms which may be the same or different and selected from oxygen atom, sulfur atom and nitrogen atom, additionally, R$^7$ may form 3–7 membered heterocyclic group by bonding together with the carbon atoms being bonded thereto on the heterocyclic group, and the newly formed 3–7 membered heterocyclic group may be interrupted by 1–3 heteroatoms which may be the same or different and selected from oxygen atom, sulfur atom and nitrogen atom;

(3) when Q is Q$^3$, then p is an integer of 1–2; and R$^7$ may form 5–7 membered heterocyclic group by bonding together with carbon atoms adjacent thereto on the heterocyclic group, and the newly formed 5–7 membered heterocyclic group may be interrupted by 1–3 heteroatoms which may be the same or different and selected from oxygen atom, sulfur atom and nitrogen atom;

(4) when Q is Q$^4$, then p is an integer of 1–2)}.

MODE FOR CARRYING OUT THE INVENTION

In the definitions of benzamide derivative represented by the general formula (I) of the present invention, the "halogen atom" means a chlorine atom, a bromine atom, an iodine atom or a fluorine atom; the "n-" means normal-; the "i-" means iso-; the "s-" means secondary-; the "t-" means tertiary-; the "$C_1$–$C_6$ alkyl" means a straight-chain or branched-chain alkyl group having 1 to 6 carbon atoms for example, methyl, ethyl, n-propyl, i-propyl, n-butyl, i-butyl, s-butyl, t-butyl, n-pentyl, neopentyl or n-hexyl; the "halo-$C_1$–$C_6$ alkyl" means a straight-chain or branched-chain alkyl group having 1 to 6 carbon atoms which is substituted with one or more halogen atoms which may be the same or different, for example, trifluoromethyl group, difluoromethyl group, perfluoroethyl group, perfluoroisopropyl group, chloromethyl group, boromomethyl group, 1-bromoethyl group or 2,3-dibromopropyl group; the "$C_1$–$C_8$ alkylene" means a straight-chain or branched-chain alkylene group having 1 to 8 carbon atoms for example, methylene, ethylene, propylene, trimethylene, dimethylmethylene, tetramethylene, isobutylene, dimethylethylene, octamethylene and the like. The "heterocyclic group" means a heterocyclic group for example, pyridyl group, pyridine-N-oxide group, pyrimidinyl group, furyl group, tetrahydrofuryl group, thienyl group, tetrahydrothienyl group, tetrahydropyranyl group, oxazolyl group, isoxazolyl group, oxadiazolyl group, thiazolyl group, isothiazolyl group, thiadiazolyl group, imidazolyl group, triazolyl group, pyrazolyl group and the like; the "condensed ring" means a condensed ring group for example, naphthalene, tetrahydronaphthalene, indene, indane, quinoline, quinazoline, chroman, isochroman, indole, indoline, benzodioxane, benzodioxole, benzofuran, dihydrobenzofuran, benzothiophene, dihydrobenzothiophene, benzoxazole, benzothiazole, benzimidazole, indazole and the like.

In some cases, the benzamide derivatives represented by the general formula (I) of the present invention contain asymmetric carbon atoms or asymemtric centers, and sometimes the benzamide derivatives contain optical isomers and diastereomers. Thus, the present invention involves the all of these optical isomers and mixtures thereof wherein said isomers are contained in any possible ratio thereof. Additionally, in some cases the benzamide derivatives represented by the general formula (I) of the present invention contain carbon-carbon double bond or carbon-nitrogen double bond, thus some times geometrical isomers are involved. Thus, the present invention involves the all of these geometrical isomers and mixtures thereof wherein said isomers are contained in any possible ratio thereof.

In the benzamide derivatives represented by the general formula (I) of the present invention, groups of preferable compounds can be exemplified in that wherein $Z^1$ is an oxygen atom; R is a hydrogen atom or methyl group; X, which may be the same or different, are halogen atoms, nitro groups, halo-$C_1$–$C_6$ alkyl groups, halo-$C_1$–$C_6$ alkoxy groups or halo-$C_1$–$C_6$ alkylthio groups; the substituted position of X is 3- or 4-position with respect to the position of carbamoyl group which is substituted in the aromatic ring; the number of the substituents X is 1 or 2; the all of $B^1$, $B^2$, $B^3$ and $B^4$ are carbon atoms, or the all of $B^1$, $B^2$ and $B^4$ are carbon atoms and $B^3$ is a nitrogen atom; Y, which may be the same or different, are halogen atoms, $C_1$–$C_6$ alkyl groups, halo-$C_1$–$C_6$ alkyl groups, halo-$C_1$–$C_6$ alkoxy groups, halo-$C_1$–$C_6$ alkylthio groups, halo-$C_1$–$C_6$ alkoxyhalo-$C_1$–$C_6$ alkoxy groups or phenyl groups which may have substituents; the substituted position of Y with respect to the position of amide group and the number m of the substituents Y is di-substitutions of 2-, 3-positions or 2-, 4-positions, or tri-substitutions of 2-, 3-, 4-positions or 2-, 4-, 5-positions; Q is a hetero ring of $Q^1$, $Q^3$, $Q^4$ or $Q^5$; W is an oxygen atom or a sulfur atom; $R^7$, which may be the same or different, are $C_1$–$C_8$ alkyl groups, $C_1$–$C_6$ alkylthio-$C_1$–$C_8$ alkyl groups, $C_1$–$C_6$ alkylsulfinyl-$C_1$–$C_8$ alkyl groups or $C_1$–$C_6$alkylsulfonyl-$C_1$–$C_8$ alkyl groups; the number p of the substituents $R^7$ is 1 or 2.

As to groups of the more preferable compounds can be exemplified in that Z is an oxygen atom; R is a hydrogen atom; X is a halogen atom, the substituted position of X is 3-position with respect to the carbamoyl group substituted in the aromatic ring; the all of $B^1$, $B^2$, $B^3$ and $B^4$ are carbon atoms; Y, which may be the same or different, are chlorine atoms, methyl groups, ethyl groups, trifluoromethyl groups, pentafluoroethyl groups, heptafluoropropyl groups, heptafluoro-i-propyl groups, trifluoromethoxy groups or 1-trifluoromethyl-2,2,2-trifluoroethoxy groups; the substituted position of Y and the number m of the substituted Y with respect to the bonded position of amide group is di-substitution at 2-, 4-position; Q is $Q^1$; W is an oxygen atom; $R^7$, which may be the same or different, are methyl groups, ethyl groups, i-propyl groups, t-butyl groups, methylthiomethyl groups, methylsulfinylmethyl groups, methylsulfonylmethyl groups, ethylthiomethyl groups, ethylsulfinylmethyl groups, or ethylsulfonylmethyl groups; the number p of the substituent $R^7$ is 1 or 2.

The benzamide derivatives represented by the general formula (I-1) of the present invention can be prepared for example by preparation methods as shown in the following scheme.

Preparation method-1

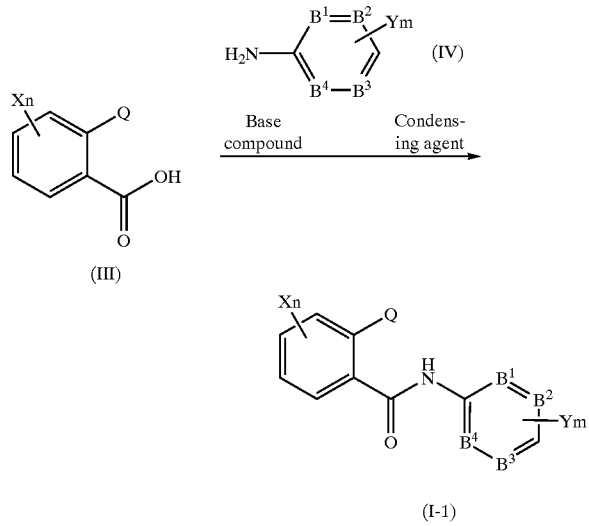

(wherein $B^1$, $B^2$, $B^3$, $B^4$, X, Y, Q, n and m are the same as defined previously).

A benzamide derivative represented by the general formula (I-1) can be prepared by reacting a benzoic acid derivative represented by the general formula (III) with an aromatic amine represented by the general formula (IV) in the presence of an inert solvent by using a condensing agent.

As to the condensing agent which can used in this reaction, diethyl cyanophosphonate (DEPC), carbonyldiimidazole (CDI), 1,3-dicyclohexylcarbodiimide (DCC), chlorocarbonates, 2-chloro-1-methylpyridinium iodide and the like can be exemplified.

As to the bases which can be used in this reaction, inorganic bases or organic bases can be exemplified. As to the inorganic bases, hydroxides of alkali metals such as sodium hydroxide, potassium hydroxide and the like, hydrides of alkali metals such as sodium hydride, potassium hydride and the like, alkali metal salts of alcohols such as potassium t-butoxide, sodium ethoxide and the like, carbonates such as potassium carbonate, sodium carbonate, sodium hydrogencarbonate and the like, as to the organic bases, triethylamine, pyridine, DBU and the like can be exemplified.

As to the inert solvents which can be used in this reaction, any solvent which does not inhibit the progress of this reaction can be used, thus aromatic hydrocarbons such as benzene, toluene, xylene and the like, halogenated hydrocarbons such as methylene chloride, chloroform, carbon tetrachloride and the like, chlorinated aromatic hydrocarbons such as chlorobenzene, dichlorobenzene and the like, chain or cyclic ethers such as diethyl ether, dioxane, tetrahydrofuran and the like, esters such as ethyl acetate and the like, amides such as dimethylformamide, dimethylacetamide and the like, dimethyl sulfoxide, 1,3-dimethyl-2-imidazolidinone, ketones such as acetone, methyl ethyl ketone and the like can be exemplified. These inert solvents can be used singly or by mixing two or more thereof.

Since, this reaction is an equimolar reaction, equimolar amounts of each one of reactants may be used, and excessive amounts of any one of reactants can be used.

This reaction can be carried out at room temperature or at refluxing temperature of the inert solvent to be used, and the reaction time varies depend on the reaction scale and reaction temperature, and the reaction time may be selected within the range of from several minutes to 48 hours.

After finished the reaction, the objective product is isolated from the reaction system containing said product in accordance with usual methods, and if necessary, said product can be purified by recrystallization, column chromatography, etc.

The benzoic acid derivative represented by the general formula (III) can be prepared by methods as disclosed in Tetrahedron, 44, 1631 (1988), Chem. Rev., 90, 879, (1990), etc.

Preparation method-2

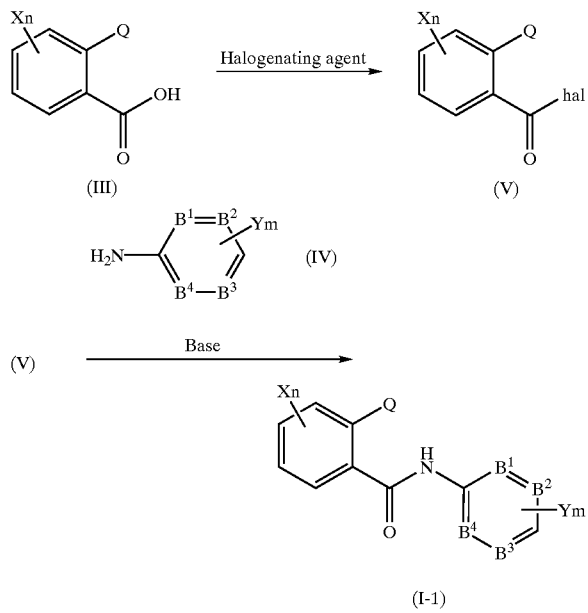

(wherein, $B^1$, $B^2$, $B^3$, $B^4$, X, Y, Q, n and m are the same as defined previously; hal means a halogen atom).

A benzamide derivative represented by the general formula (I-1) can be prepared by reacting a benzoic acid derivative represented by the general formula (III) in the presence or absence of an inert solvent by using a halogenating agent to obtain a benzoyl halide derivative (V), next, by reacting said halogenated benzoyl derivative (V) with an aromatic amine represented by the general formul (IV) in the presence of an inert solvent by using a base.

2-1. Reaction of the General Formula (III)→the General Formula (V)

As to the halogenating agents which can be used in this reaction, halogenating agents such as thionyl chloride, phosphorus oxychloride, phosphorus trichloride, phosphorus tribromide, phosphorus oxybromide, dichloromethylmethyl ether and the like can be exemplified. Using amount of the halogenating agent may be selected suitably from the range of 1–100 equivalents thereof to an equivant amount of a benzoic acid derivative represented by the general formula (III).

As to the inert solvents which can be used in this reaction, any solvent which does not inhibit the progress of this reaction can be used, thus aromatic hydrocarbons such as benzene, toluene, xylene and the like, halogenated hydrocarbons such as methylene chloride, chloroform, carbon tetrachloride and the like, chlorinated aromatic hydrocarbons such as chlorobenzene, dichlorobenzene and the like, esters such as ethyl acetate and the like can be exemplified. These inert solvents can be used singly or by mixing two or more thereof.

As to the reaction temperature, this reaction can be carried out in a temperature range of room temperature to the boiling point of the inert solvent used. Although the reaction time varies depend on the reaction scale and reaction temperature, etc., it may be selected suitably within the range of a few minutes to 48 hours.

After finished the reaction, the objective product is isolated or without isolated from the reaction system containing said product in accordance with usual methods, then said objective product may be used in the next reaction step.

2-2. Reaction of the General Formula (V)→the General Formula (I-1)

As to the bases which can be used in this reaction, the bases disclosed in Preparation method-1 can be used, and as to the inert solvents, those of disclosed in Preparation method-1 can be used. These inert solvents can be used singly or by mixing 2 or more thereof.

Since, this reaction is an equimolar reaction, each one of these reactants may be used in equimolar amounts, and excessive amounts of any one of these reactants can be also used.

As to the reaction temperature, this reaction can be carried out in a temperature range of room temperature to the boiling point of the inert solvent used. Although the reaction time varies depend on the reaction scale and reaction temperature, etc., it may be selected suitably within the range of a few minutes to 48 hours.

After finished the reaction, the objective product is isolated from the reaction system containing said product in accordance with usual methods, if necessary, said objective product can be purified by recrystallization, a column chromatography and the like.

Preparation method-3

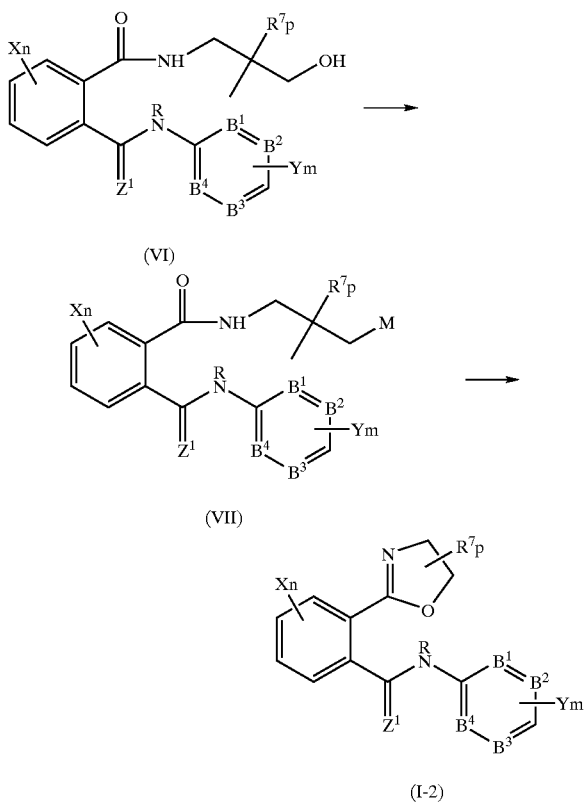

(wherein, R, R$^7$, B$^1$, B$^2$, B$^3$, B$^4$, X, Y, Z$^1$, n and m are the same as defined previously; M is a halogen atom or R$^{12}$SO$_3$— (wherein, R$^{12}$ is a C$_1$–C$_6$ alkyl group such as a methyl group and the like, or a phenyl group which may have a substituent such as a methyl group and the like at the para-position)).

A compound represented by the general formula (VII) is prepared by reacting a phthalic acid diamide represented by the general formula (VI) with halogenating agent or a sulfonic acid esterifying agent in the presence or absence of an inert solvent, next, by reacting under heating condition or by using a base, a benzamide derivative represented by the general formula (I-2) can be prepared.

3-1 Reaction of the General Formula (VI)→the General Formula (VII)

As to halogenating agents which can be used in this reaction, diethylaminosulfur trifluoride (DAST), thionyl chloride, phosphorus oxychloride or a combination of triphenylphosphine with carbon tetrabromide or with carbon tetrachloride can be exemplified.

As to sulfonic acid esterifying agents which can be used in this reaction, sulfonyl halides such as methanesulfonyl chloride, p-toluenesulfonyl chloride and the like can be exemplified.

As to bases which can be used in this reaction, the bases disclosed in Preparation method-1 can be used, and as to the inert solvents, in addition to those of disclosed in Preparation method-1, inert solvents such as pyridine and the like can be used. These inert solvents can be used singly or by mixing 2 or more thereof.

Since, this reaction is an equimolar reaction, equimolar amounts of each one of reactants may be used, and excessive amounts of any one of reactants can be also used.

As to the reaction temperature, this reaction can be carried out in a temperature range of −20° C. to the boiling point of the inert solvent used. Although the reaction time varies depend on the reaction scale and reaction temperature, etc., it may be selected suitably within the range of several minutes to 48 hours.

Among phthalic acid diamide derivatives represented by the general formula (VII), the compounds wherein M is R$^{12}$SO$_3$— are novel derivatives and perform insecticidal activities.

Phthalic acid diamide derivatives represented by the general formula (VI) can be prepared by the method according to the disclosure in JP-A-11-240857.

3-2. Reaction of the General Formula (VII)→the General Formula (I-2)

As to bases and inert solvents which can be used in this reaction, the bases and the inert solvents disclosed in Preparation method-1 can be used, and these inert solvents can be used singly or by mixing 2 or more thereof.

Since, this reaction is an equimolar reaction, equimolar amounts of each one of reactants may be used, and excessive amounts of any one of the reactants can be also used.

As to the reaction temperature, this reaction can be carried out in a temperature range of −20° C. to the boiling point of the inert solvent used. Although the reaction time varies depend on the reaction scale and reaction temperature, etc., it may be selected suitably within the range of several minutes to 48 hours.

Preparation method-4

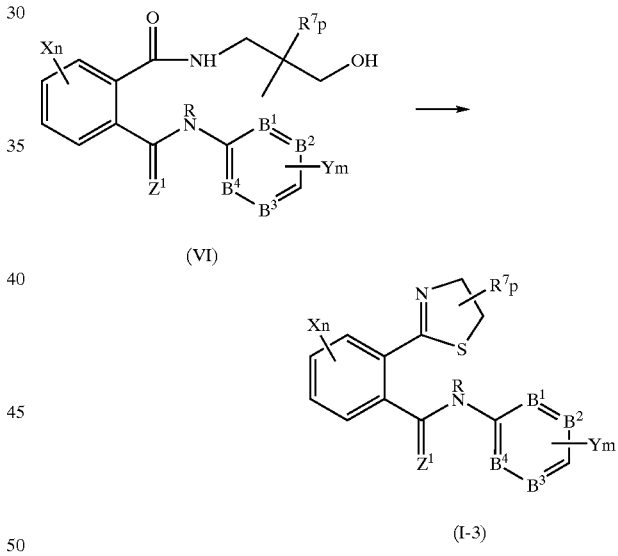

(wherein, R, R$^7$, B$^1$, B$^2$, B$^3$, B$^4$, X, Y, Z$^1$, n and m are the same as defined previously).

A benzamide derivative represented by the general formula (I-3) can be prepared by reacting a phthalic acid diamide derivative (VI) with a sulfurizing agent in the presence of an inert solvent.

As to the sulfurizing agent which can be used in this reaction, phosphorus pentasulfide and the like can be exemplified, and using amount of the sulfurizing agent may be selected suitably from 1–5 equimolar amounts to an equimolar quantity of the phthalic acid diamide derivative represented by the general formula (VI).

As to the inert solvents which can be used in this reaction, in addition to the inert solvents disclosed in Preparation method-1, water can be also used, and these inert solvents can be used singly or by mixing 2 or more thereof.

As to the reaction temperature, this reaction can be carried out in a temperature range of room temperature to the boiling point of the inert solvent used. Although the reaction time varies depend on the reaction scale and reaction temperature, etc., it may be selected suitably within the range of a few minutes to 48 hours.

Preparation method-5

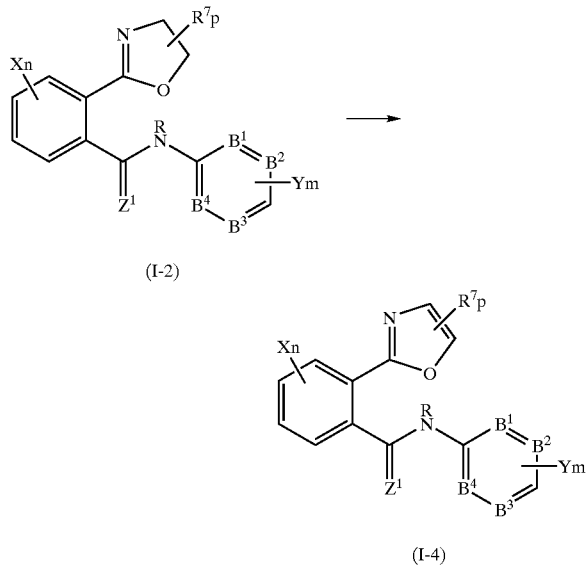

(wherein, R, $R^7$, $B^1$, $B^2$, $B^3$, $B^4$, X, Y, Z, n and m are the same as defined previously).

A benzamide derivative represented by the general formula (I-4) can be prepared by reacting a benzamide derivative represented by the general formula (I-2) in the presence of an inert solvent by using a catalyst.

As to the catalyst which can be used in this reaction, such as nickel oxide and the like can be exemplified, and the amount of the catalyst used may be selected suitably in the range of 1–20 equivalents per equivalent of the benzamide derivative of the general formula (I-2).

As to the inert solvents which can be used in this reaction, those disclosed in Preparation method-1 can be used, and these inert solvents can be used singly or by mixing 2 or more thereof.

As to the reaction temperature, this reaction can be carried out in a temperature range of room temperature to the boiling point of the inert solvent used. Although the reaction time varies depend on the reaction scale and reaction temperature, etc., it may be selected suitably within the range of a few minutes to 48 hours.

Typical examples of benzamide derivatives represented by the general formula (I) are exemplified in the following Table 1 to Table 4. However, scope of the present invention is not restricted within these examples.

In these Tables, "Me" means methyl group, "Et" means ethyl group, "Pr" means propyl group, "Bu" means butyl group, "Ph" means phenyl group, "Bn" means benzyl group, "c-" means alicyclic group, "(R)" and "(S)" respectively means stereo isomerism at the corresponding substituted position.

The general formula (I-5) is shown as follows:

TABLE 1

R=H, Z=O, except for $Z^1$ as noted specifically

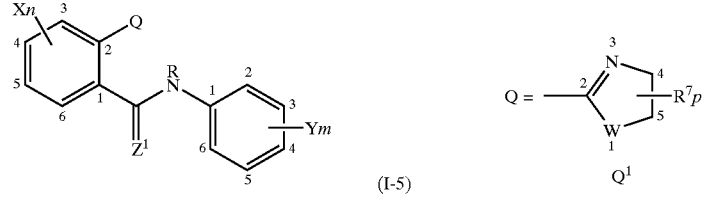

| No. | Xn | Q | W | $R^7_p$ | Ym | m.p.(° C.) |
|---|---|---|---|---|---|---|
| 1-1 | H | $Q^1$ | O | 4-(4-t-Bu-Ph) | 2-Me-4-$CF_2CF_3$ | 73–74 |
| 1-2 | H | $Q^1$ | O | 4,4-$(Me)_2$ | 2-Me-4-$CF_2CF_3$ | 115–116 |
| 1-3 | H | $Q^1$ | O | 4-Bn | 2-Me-4-$CF_2CF_3$ | 42–43 |
| 1-4 | 6-Cl | $Q^1$ | O | 4,4-$(Me)_2$ | 2-Me-4-$CF_2CF_3$ | 166–167 |
| 1-5 | 6-Cl | $Q^1$ | O | 4-Et | 2-Me-4-$CF_2CF_3$ | 107–109 |
| 1-6 | 6-Cl | $Q^1$ | O | 4,4-$(Me)_2$ | 2-Me-4-$CF_2CF_3$ | 58 |
| 1-7 | 6-Cl | $Q^1$ | O | 4-Me(R) | 2-Me-4-$CF_2CF_3$ | 123 |
| 1-8 | 6-Cl | $Q^1$ | O | 4-Me(S) | 2-Me-4-$CF_2CF_3$ | 123 |
| 1-9 | 6-Cl | $Q^1$ | O | 4-(4-Ph-Ph) | 2-Me-4-$CF_2CF_3$ | 188 |
| 1-10 | 6-Cl | $Q^1$ | O | 4-Ph | 2-Me-4-$CF_2CF_3$ | 66–67 |
| 1-11 | 3-Cl | $Q^1$ | O | 4-(4-t-Bu-Ph) | 2-Me-4-$CF_2CF_3$ | 189–190 |
| 1-12 | 3-Cl | $Q^1$ | O | 4-(4-Ph-Ph) | 2-Me-4-$CF_2CF_3$ | 201–202 |
| 1-13 | 3-Cl | $Q^1$ | O | 4-Me(R) | 2-Me-4-$CF_2CF_3$ | 136 |
| 1-14 | 3-Cl | $Q^1$ | O | 4-Me(S) | 2-Me-4-$CF_2CF_3$ | 136 |
| 1-15 | 3-Cl | $Q^1$ | O | 4-Ph | 2-Me-4-$CF_2CF_3$ | 119–121 |
| 1-16 | 3-Cl | $Q^1$ | O | 4,4-$(Me)_2$ | 2-Me-4-$CF_2CF_3$ | 164–165 |
| 1-17 | 3-Cl | $Q^1$ | O | 4,4-$(Me)_2$ | 2-Me-4-$CF(CF_3)_2$ | 191–193 |
| 1-18 | 3-Cl | $Q^1$ | O | 5-Ph | 2-Me-4-$CF_2CF_3$ | 206 |
| 1-19 | 6-I | $Q^1$ | O | 4-Me(R) | 2-Me-4-$CF_2CF_3$ | 103–104 |
| 1-20 | 3-I | $Q^1$ | O | 4,4-$(Me)_2$ | 2-Me-4-$OCF_3$ | 173 |
| 1-21 | 3-I | $Q^1$ | O | 4-Me(R) | 2-Me-4-$CF_2CF_3$ | 123–124 |
| 1-22 | 3-I | $Q^1$ | O | 4-Me(S) | 2-Me-4-$CF_2CF_3$ | 122–123 |
| 1-23 | 3-I | $Q^1$ | O | 4,4-$(Me)_2$ | 2-Me-4-$CF_2CF_3$ | 192–193 |
| 1-24 | 3-I | $Q^1$ | O | 4,4-$(Me)_2$ | 2-Et-4-$CF_2CF_3$ | |

TABLE 1-continued

R=H, Z=O, except for $Z^1$ as noted specifically (I-5)

$Q = Q^1$

| No. | Xn | Q | W | $R^7_p$ | Ym | m.p.(° C.) |
|---|---|---|---|---|---|---|
| 1-25 | 3-I | $Q^1$ | O | 4,4-(Me)$_2$ | 2-F-4-CF(CF$_3$)$_2$ | |
| 1-26 | 3-I | $Q^1$ | O | 4,4-(Me)$_2$ | 2-Cl-4-CF$_2$CF$_3$ | |
| 1-27 | 3-I | $Q^1$ | O | 4,4-(Me)$_2$ | 2-Me-3-F-4-CF(CF$_3$)$_2$ | |
| 1-28 | 3-I | $Q^1$ | O | 4,4-(Me)$_2$ | 2-F-4-CF$_2$CF$_3$ | |
| 1-29 | 3-I | $Q^1$ | O | 4,4-(Me)$_2$ | 2-Me-5-F-4-CF(CF$_3$)$_2$ | |
| 1-30 | 3-I | $Q^1$ | O | 4,4-(Me)$_2$ | 2-Et-4-CF(CF$_3$)$_2$ | |
| 1-31 | 3-I | $Q^1$ | O | 4,4-(Me)$_2$ | 2-Cl-4-CF(CF$_3$)$_2$ | |
| 1-32 | 3-I | $Q^1$ | O | 4-CH$_2$SMe | 2-Me-4-CF$_2$CF$_3$ | |
| 1-33 | 3-I | $Q^1$ | O | 4-CH$_2$SMe | 2-Me-4-CF(CF$_3$)$_2$ | |
| 1-34 | 3-I | $Q^1$ | O | 4-CH$_2$SMe | 2-Me-4-OCF$_3$ | |
| 1-35 | 3-I | $Q^1$ | O | 4-CH$_2$SMe | 2-Me-4-SCF$_3$ | |
| 1-36 | 3-I | $Q^1$ | O | 4-CH$_2$SMe | 2-Et-4-CF$_2$CF$_3$ | |
| 1-37 | 3-I | $Q^1$ | O | 4-CH$_2$SMe | 2-F-4-CF(CF$_3$)$_2$ | |
| 1-38 | 3-I | $Q^1$ | O | 4-CH$_2$SMe | 2-Cl-4-CF$_2$CF$_3$ | |
| 1-39 | 3-I | $Q^1$ | O | 4-CH$_2$SMe | 2-Me-3-F-4-CF(CF$_3$)$_2$ | |
| 1-40 | 3-I | $Q^1$ | O | 4-CH$_2$SOMe | 2-Me-4-CF$_2$CF$_3$ | |
| 1-41 | 3-I | $Q^1$ | O | 4-CH$_2$SOMe | 2-Me-4-CF(CF$_3$)$_2$ | |
| 1-42 | 3-I | $Q^1$ | O | 4-CH$_2$SOMe | 2-Me-4-OCF$_3$ | |
| 1-43 | 3-I | $Q^1$ | O | 4-CH$_2$SOMe | 2-Me-4-SCF$_3$ | |
| 1-44 | 3-I | $Q^1$ | O | 4-CH$_2$SOMe | 2-Et-4-CF$_2$CF$_3$ | |
| 1-45 | 3-I | $Q^1$ | O | 4-CH$_2$SOMe | 2-F-4-CF(CF$_3$)$_2$ | |
| 1-46 | 3-I | $Q^1$ | O | 4-CH$_2$SOMe | 2-Cl-4-CF$_2$CF$_3$ | |
| 1-47 | 3-I | $Q^1$ | O | 4-CH$_2$SOMe | 2-Me-3-F-4-CF(CF$_3$)$_2$ | |
| 1-48 | 3-I | $Q^1$ | O | 4-CH$_2$SO$_2$Me | 2-Me-4-CF$_2$CF$_3$ | |
| 1-49 | 3-I | $Q^1$ | O | 4-CH$_2$SO$_2$Me | 2-Me-4-CF(CF$_3$)$_2$ | |
| 1-50 | 3-I | $Q^1$ | O | 4-CH$_2$SO$_2$Me | 2-Me-4-OCF$_3$ | |
| 1-51 | 3-I | $Q^1$ | O | 4-CH$_2$SO$_2$Me | 2-Me-4-SCF$_3$ | |
| 1-52 | 3-I | $Q^1$ | O | 4-CH$_2$SO$_2$Me | 2-Et-4-CF$_2$CF$_3$ | |
| 1-53 | 3-I | $Q^1$ | O | 4-CH$_2$SO$_2$Me | 2-F-4-CF(CF$_3$)$_2$ | |
| 1-54 | 3-I | $Q^1$ | O | 4-CH$_2$SO$_2$Me | 2-Cl-4-CF$_2$CF$_3$ | |
| 1-55 | 3-I | $Q^1$ | O | 4-CH$_2$SO$_2$Me | 2-Me-3-F-4-CF(CF$_3$)$_2$ | |
| 1-56 | 3-I | $Q^1$ | O | 4-Me-4-CH$_2$SMe | 2-Me-4-CF$_2$CF$_3$ | |
| 1-57 | 3-I | $Q^1$ | O | 4-Me-4-CH$_2$SMe | 2-Me-4-CF(CF$_3$)$_2$ | 163–164 |
| 1-58 | 3-I | $Q^1$ | O | 4-Me-4-CH$_2$SMe | 2-Me-4-OCF$_3$ | |
| 1-59 | 3-I | $Q^1$ | O | 4-Me-4-CH$_2$SMe | 2-Me-4-SCF$_3$ | |
| 1-60 | 3-I | $Q^1$ | O | 4-Me-4-CH$_2$SMe | 2-Et-4-CF$_2$CF$_3$ | |
| 1-61 | 3-I | $Q^1$ | O | 4-Me-4-CH$_2$SMe | 2-F-4-CF(CF$_3$)$_2$ | |
| 1-62 | 3-I | $Q^1$ | O | 4-Me-4-CH$_2$SMe | 2-Cl-4-CF$_2$CF$_3$ | |
| 1-63 | 3-I | $Q^1$ | O | 4-Me-4-CH$_2$SMe | 2-Me-3-F-4-CF(CF$_3$)$_2$ | |
| 1-64 | 3-I | $Q^1$ | O | 4-Me-4-CH$_2$SOMe | 2-Me-4-CF$_2$CF$_3$ | |
| 1-65 | 3-I | $Q^1$ | O | 4-Me-4-CH$_2$SOMe | 2-Me-4-CF(CF$_3$)$_2$ | 80–82 |
| 1-66 | 3-I | $Q^1$ | O | 4-Me-4-CH$_2$SOMe | 2-Me-4-OCF$_3$ | |
| 1-67 | 3-I | $Q^1$ | O | 4-Me-4-CH$_2$SOMe | 2-Me-4-SCF$_3$ | |
| 1-68 | 3-I | $Q^1$ | O | 4-Me-4-CH$_2$SOMe | 2-Et-4-CF$_2$CF$_3$ | |
| 1-69 | 3-I | $Q^1$ | O | 4-Me-4-CH$_2$SOMe | 2-F-4-CF(CF$_3$)$_2$ | |
| 1-70 | 3-I | $Q^1$ | O | 4-Me-4-CH$_2$SOMe | 2-Cl-4-CF$_2$CF$_3$ | |
| 1-71 | 3-I | $Q^1$ | O | 4-Me-4-CH$_2$SOMe | 2-Me-3-F-4-CF(CF$_3$)$_2$ | |
| 1-72 | 3-I | $Q^1$ | O | 4-Me-4-CH$_2$SO$_2$Me | 2-Me-4-CF$_2$CF$_3$ | |
| 1-73 | 3-I | $Q^1$ | O | 4-Me-4-CH$_2$SO$_2$Me | 2-Me-4-CF(CF$_3$)$_2$ | 108–110 |
| 1-74 | 3-I | $Q^1$ | O | 4-Me-4-CH$_2$SO$_2$Me | 2-Me-4-OCF$_3$ | |
| 1-75 | 3-I | $Q^1$ | O | 4-Me-4-CH$_2$SO$_2$Me | 2-Me-4-SCF$_3$ | |
| 1-76 | 3-I | $Q^1$ | O | 4-Me-4-CH$_2$SO$_2$Me | 2-Et-4-CF$_2$CF$_3$ | |

TABLE 1-continued

R=H, Z=O, except for $Z^1$ as noted specifically

Structure (I-5): Xn substituted benzene with Q at position 2, connected via C(=Z¹)-N(R)- to another phenyl with Ym substituent.

$Q^1$ = 5-membered ring with N at position 3, W at position 1, bearing $R^7_p$ at positions 4,5.

| No. | Xn | Q | W | $R^7_p$ | Ym | m.p.(° C.) |
|---|---|---|---|---|---|---|
| 1-77 | 3-I | $Q^1$ | O | 4-Me-4-CH$_2$SO$_2$Me | 2-F-4-CF(CF$_3$)$_2$ | |
| 1-78 | 3-I | $Q^1$ | O | 4-Me-4-CH$_2$SO$_2$Me | 2-Cl-4-CF$_2$CF$_3$ | |
| 1-79 | 3-I | $Q^1$ | O | 4-Me-4-CH$_2$SO$_2$Me | 2-Me-3-F-4-CF(CF$_3$)$_2$ | |
| 1-80 | 3-I | $Q^1$ | O | 4-Me-4-CH$_2$SO$_2$Me | 2-Me-4-CF$_2$CF$_3$ | |
| 1-81 | 3-I | $Q^1$ | O | 4-(CH$_2$)$_4$-4 | 2-Me-4-CF(CF$_3$)$_2$ | 187–188 |
| 1-82 | 3-I | $Q^1$ | O | 4,4-(Me)$_2$ | 2-Me-4-CF(CF$_3$)$_2$ | 171–172 |
| 1-83 | 6-Cl | $Q^1$ | O | H | 2-Me-4-CF$_2$CF$_3$ | |
| 1-84 | 3-Cl | $Q^1$ | S | 4-Me | 2-Me-4-CF$_2$CF$_3$ | 140–144 |
| 1-85 | 3-Cl | $Q^1$ | S | 4,4-(Me)$_2$ | 2-Me-4-CF(CF$_3$)$_2$ | 152–153 |
| 1-86 | 3-I | $Q^1$ | S | 4,4-(Me)$_2$ | 2-Me-4-CF(CF$_3$)$_2$ | 135–136 |
| 1-87 | 3-I | $Q^1$ | NMe | 4-CH$_2$SMe | 2-Me-4-CF(CF$_3$)$_2$ | |
| 1-88 | 3-I | $Q^1$ | S | 4-CH$_2$SMe | 2-Me-4-CF(CF$_3$)$_2$ | ($Z^1$=S) |
| 1-89 | 3-I | $Q^1$ | NMe | 4-CH$_2$SMe | 2-Me-4-CF(CF$_3$)$_2$ | ($Z^1$=S) |
| 1-90 | 3-I | $Q^1$ | O | 4-Me-4-CH$_2$SEt | 2-Me-4-CF(CF$_3$)$_2$ | 60–62 |
| 1-91 | 6-I | $Q^1$ | O | 4-Me-4-CH$_2$SEt | 2-Me-4-CF(CF$_3$)$_2$ | 52–55 |
| 1-92 | 3-I | $Q^1$ | O | 4-Me-4-CH$_2$SO$_2$Et | 2-Me-4-CF(CF$_3$)$_2$ | 80–82 |
| 1-93 | 3-I | $Q^1$ | O | 4-Me-4-CH$_2$S-(4-t-Bu-Ph) | 2-Me-4-CF(CF$_3$)$_2$ | 140–141 |

TABLE 2

R=H, $Z^1$=O $Q^2$ = 6-membered ring with N at 3, W at 1, $R^7_p$ substituent.
$Q^3$ = 5-membered ring with N at 3, W at 1, $R^7_p$ at position 4.
$Q^4$ = 5-membered ring with N at 2, W at 1, $R^7_p$ at position 4.

| No. | Xn | Q | W | $R^7_p$ | Ym | m.p. (° C.) |
|---|---|---|---|---|---|---|
| 2-1 | 3-I | $Q^2$ | O | 4-CH$_2$SMe | 2-Me-4-CF(CF$_3$)$_2$ | |
| 2-2 | 3-I | $Q^2$ | S | 4-CH$_2$SMe | 2-Me-4-CF(CF$_3$)$_2$ | |
| 2-3 | 3-I | $Q^2$ | NMe | 4-CH$_2$SMe | 2-Me-4-CF(CF$_3$)$_2$ | |
| 3-1 | 6-Cl | $Q^3$ | O | H | 2-Me-4-CF(CF$_3$)$_2$ | 197–200 |
| 3-2 | 6-Cl | $Q^3$ | O | 4-Me | 2-Me-4-CF(CF$_3$)$_2$ | 187 |
| 3-3 | 3-Cl | $Q^3$ | O | 4-Me | 2-Me-4-CF$_2$CF$_3$ | |
| 3-4 | 3-I | $Q^3$ | O | 4-CH$_2$SMe | 2-Me-4-CF(CF$_3$)$_2$ | |
| 3-5 | 3-I | $Q^3$ | S | 4-CH$_2$SMe | 2-Me-4-CF(CF$_3$)$_2$ | |
| 3-6 | 3-I | $Q^3$ | NMe | 4-CH$_2$SMe | 2-Me-4-CF(CF$_3$)$_2$ | |
| 4-1 | 3-Cl | $Q^4$ | O | 2-t-Bu | 2-Me-4-OCF$_3$ | 140 |
| 4-2 | 3-I | $Q^4$ | O | 2-CH$_2$SMe | 2-Me-4-CF(CF$_3$)$_2$ | |
| 4-3 | 3-I | $Q^4$ | S | 2-CH$_2$SMe | 2-Me-4-CF(CF$_3$)$_2$ | |
| 4-4 | 3-I | $Q^4$ | NMe | 2-CH$_2$SMe | 2-Me-4-CF(CF$_3$)$_2$ | |
| 4-5 | 3-I | $Q^4$ | O | 2-CH$_2$SMe | 2-Me-4-CF(CF$_3$)$_2$ | |
| 4-6 | 3-I | $Q^4$ | S | 2-CH$_2$SMe | 2-Me-4-CF(CF$_3$)$_2$ | |
| 4-7 | 3-I | $Q^4$ | NMe | 2-CH$_2$SMe | 2-Me-4-CF(CF$_3$)$_2$ | |

TABLE 3

R=H, $Z^1$=O $Q^5$, $Q^6$ = triazole rings with $R^7$ substituent; $Q^7$, $Q^8$ = tetrazole rings with $R^8$ substituent.

| No. | Xn | Q | W | $R^7$ or $R^8$ | Ym | m.p.(° C.) |
|---|---|---|---|---|---|---|
| 5-1 | H | $Q^5$ | O | t-Bu | 2-Me-4-CF$_2$CF$_3$ | 135 |
| 5-2 | H | $Q^5$ | O | t-Bu | 2-Me-4-OCF$_3$ | 115 |
| 5-3 | 3-Cl | $Q^5$ | O | t-Bu | 2-Me-4-OCF$_3$ | 100 |
| 5-4 | 3-I | $Q^5$ | O | CH$_2$SMe | 2-Me-4-CF(CF$_3$)$_2$ | |
| 5-5 | 3-I | $Q^5$ | S | CH$_2$SMe | 2-Me-4-CF(CF$_3$)$_2$ | |
| 5-6 | 3-I | $Q^5$ | NMe | CH$_2$SMe | 2-Me-4-CF(CF$_3$)$_2$ | |
| 6-1 | H | $Q^6$ | O | 4-Cl-Ph | 2-Me | 218–219 |
| 6-2 | H | $Q^6$ | O | 4-Cl-Ph | 2-Me-4-CF$_2$CF$_3$ | 141–148 |
| 6-3 | H | $Q^6$ | O | i-Pr | 2-Me | 159–165 |
| 6-4 | H | $Q^6$ | O | i-Pr | 2-Me-4-Cl | 300< |
| 6-5 | H | $Q^6$ | O | i-Pr | 2-Me-4-OCF$_3$ | 159 |
| 6-6 | 3-I | $Q^6$ | O | CH$_2$SMe | 2-Me-4-CF(CF$_3$)$_2$ | |
| 6-7 | 3-I | $Q^6$ | S | CH$_2$SMe | 2-Me-4-CF(CF$_3$)$_2$ | |
| 6-8 | 3-I | $Q^6$ | NMe | CH$_2$SMe | 2-Me-4-CF(CF$_3$)$_2$ | |
| 7-1 | 3-I | $Q^7$ | — | Me | 2-Me-4-CF(CF$_3$)$_2$ | |
| 8-1 | 3-I | $Q^8$ | — | Me | 2-Me-4-CF(CF$_3$)$_2$ | |

General formula (I-6):

TABLE 4

R=H, Z$^1$=O (I-6)

| No. | Xn | Q | W | R$^7_p$ or R$^8$ | Ym | m.p.(° C.) |
|---|---|---|---|---|---|---|
| 9-1 | 3-F | Q$^1$ | O | 4-CH$_2$SMe | 6-Me-4-CF(CF$_3$)$_2$ | |
| 9-2 | 3-I | Q$^1$ | O | 4,4-(Me)$_2$ | 6-Me-4-OCH(CF$_3$)$_2$ | 204–205 |
| 9-3 | 3-Cl | Q$^1$ | O | 2-Me | 4-Me-2-CF$_2$CH$_3$ | |
| 9-4 | 3-I | Q$^1$ | S | 4,4-(Me)$_2$ | 6-Cl-2-OCHF$_2$ | |
| 9-5 | 3-I | Q$^1$ | O | 4-Me-4-CH$_2$SMe | 4-Me-2-CF(CF$_3$)$_2$ | |
| 9-6 | 3-NO$_2$ | Q$^1$ | O | 4,4-(Me)$_2$ | 6-MeO-2-CF(CF$_3$)$_2$ | |
| 9-7 | 3-Br | Q$^1$ | O | 4-Cl-Ph | 6-Cl-2-CF(CF$_3$)$_2$ | |
| 9-8 | 3-I | Q$^1$ | O | 4,4-(Me)$_2$ | 6-Me-2-OCF$_2$CF$_2$H | |
| 9-9 | 3-I | Q$^1$ | O | 4-CH$_2$OMe | 6-Me-2-OCF$_2$CHFOCF$_3$ | |
| 9-10 | 3-Cl | Q$^3$ | O | 4-t-Bu | 6-Me-2-OCF$_2$CF$_2$CF$_3$ | |
| 9-11 | 3-Cl | Q$^4$ | O | 2-i-Pr | 4-Me-2-OCF$_2$Br | |
| 9-12 | 3-I | Q$^5$ | O | CH$_2$SMe | 4-Me-2-OCF$_2$CF$_2$CF$_3$ | |
| 9-13 | 3-I | Q$^6$ | O | CH$_2$SMe | 6-Me-4-CF$_2$CF$_3$ | |
| 9-14 | 3-I | Q$^6$ | NMe | CH$_2$SMe | 6-Cl-2-CF(CF$_3$)$_2$ | |
| 9-15 | 3-I | Q$^7$ | — | Me | 2-CF(CF$_3$)$_2$ | |
| 9-16 | 3-I | Q$^8$ | — | Me | 2-OCH(CF$_3$)$_2$ | |

The agricultural and horticultural insecticides containing the benzamide derivative of formula (I) of the present invention as an active ingredient are suitable for controlling various insect pests such as agrohorticultural insect pests, stored grain insect pests, sanitary insect pests, nematodes, etc., which are injurious to paddy rice, fruit trees, vegetables, other crops, flowers, ornamental plants, etc. They have a marked insecticidal effect, for example, on LEPIDOPTERA including summer fruit tortrix (*Adoxophes orana fasciata*), smaller tea tortrix (Adoxphyes sp), Manchurian fruit moth (*Grapholita inopinata*), oriental fruit moth (*Grapholita molesta*), soybean pod border (*Leguminovora glycinivorella*), mulberry leafroller (*Olethreutes mori*), tea leafroller (*Caloptilia thevivora*), Caloptilia sp. (*Caloptilia zachrysa*), apple leafminer (*Phyllonorycter ringoniella*), pear barkminer (*Spulerrina astaurota*), common white (*Piers rapae crucivora*), tobacco budworm (Heliothis sp.), codling moth (*Laspey resia pomonella*), diamondback moth (*Plutella xylostella*), apple fruit moth (*Argyresthia conjugella*), peach fruit moth (*Carposina niponensis*), rice stem borer (*Chilo suppressalis*), rice leafroller (*Cnaphalocrocis medinalis*), tobacco moth (*Ephestia elutella*), mulberry pyralid (*Glyphodes pyloalis*), yellow rice borer (*Scirpophaga incertulas*), rice skipper (*Parnara guttata*), rice armyworm (*Pseudaletia separata*), pink borer (*Sesamia inferens*), common cutworm (*Spodoptera litura*), beet armyworm (*Spodoptera exigua*), etc.; HEMIPTERA including aster leafhopper (*Macrosteles fascifrons*), green rice leafhopper (*Nephotettix cincticepts*), brown rice planthopper (*Nilaparvata lugens*), whitebacked rice planthopper (*Sogatella furcifera*), citrus psylla (*Diaphorina citri*), grape whitefly (*Aleurolibus taonabae*), sweetpotato whitefly (*Bemisia tabaci*), greenhouse whitefly (*Trialeurodes vaporariorum*), turnup aphid (*Lipaphis erysimi*), green peach aphid (*Myzus persicae*), Indian wax scale (*Ceroplastes ceriferus*), cottony citrus scale (*Pulvinaria aurantii*), camphor scale (*Pseudaonidia duplex*), san Jose scale (*Comstockaspis perniciosa*), arrowhead scale (*Unapsis yanonensis*), etc.; TYLENCHIDA including soybean beetle (*Anomala rufocuprea*), Japanese beetle (*Popillia japonica*), tobacco beetle (*Lasioderma serricorne*), powderpost beetle (*Lyctus brunneus*), twenty-eight-spotted ladybird (*Epilachna vigintiotopunctata*), azuki bean weevil (*Callosobruchus chinensis*), vegetable weevil (*Listroderes costirostris*), maize weevil (*Sitophilus zeamais*), boll weevil (*Anthonomus gradis gradis*), rice water weevil (*Lissorhoptrus oryzophilus*), cucurbit leaf beetle (*Aulacophora femoralis*), rice leaf beetle (*Oulema oryzae*), striped flea beetle (*Phyllotreta striolata*), pine shoot beetle (*Tomicus piniperda*), Colorado potato beetle (*Leptinotarsa decemlineata*), Mexican bean beetle (*Epilachna varivestis*), corn rootworm (Diabrotica sp.), etc.; DIPTERA including (*Dacus(Zeugodacus) cucurbitae*), oriental fruit fly (*Dacus (Bactrocera) dorsalis*), rice leafminer (*Agnomyza oryzae*), onion maggot (*Delia antiqua*), seedcorn maggot (*Delia platura*), soybean pod gall midge (Asphondylia sp.), house fly (*Musca domestica*), house mosquito (*Culex pipiens pipiens*), etc.; and TYLENCHIDA including coffee root-lesion nematode (*Pratylenchus coffeae*), potato cyst nematode (*Globodera rostochiensis*), root-knot nematode (Meloidogyne sp.), citrus nematode (*Tylenchulus semipenetrans*), Aphelenchus sp. (*Aphelenchus avenae*), chrysanthemum foliar (*Aphelenchoides ritzemabosi*), etc.

The agricultural and horticultural insecticide containing the benzamide derivative represented by formula (I) of the present invention has a marked controlling effect on the above-exemplified insect pests, sanitary pests and/or nematodes, which are injurious to paddy field crops, upland crops, fruit trees, vegetables and other crops, flowers and ornament plants, and the like. Therefore, the desired effect of the agrohorticultural insecticide of the present invention can be exhibited by applying the insecticide to the paddy field water, stalks and leaves or soil of paddy field, upland field, fruit trees, vegetables, other crops or flowers and ornament plants at a season at which the insect pests, sanitary pests or nematodes are expected to appear, before their appearance or at the time when their appearance is confirmed.

In general, the agricultural and horticultural insecticide of the present invention is used after being prepared into conveniently usable forms according to ordinary manner for preparation of agrochemicals.

That is, the benzamide derivative of formula (I) and an appropriate carrier are blended optionally together with an adjuvant in a proper proportion and prepared into a suitable preparation form such as suspension, emulsifiable concentrate, soluble concentrate, wettable powder, granules, dust or tablets through dissolution, separation, suspension, mixing, impregnation, adsorption or sticking.

The inert carrier used in the present invention may be either solid or liquid. As the solid carrier, soybean flour, cereal flour, wood flour, bark flour, saw dust, powdered tobacco stalks, powdered walnut shells, bran, powdered cellulose, extraction residues of vegetables, powdered synthetic polymers or resins, clay (e.g. kaolin, bentonite and acid clay), talc (e.g. talc and pyrophyllite), silica materials (e.g. diatomaceous earth, siliceous sand, mica, white carbon, i.e. synthetic high-dispersion silicic acid, also called finely divided hydrated silica or hydrated silicic acid, some of the commercially available products contain calcium silicate as the major component), activated carbon, powdered sulfur, pumice, calcined diatomaceous earth, ground brick, fly ash, sand, calcium carbonate, calcium phosphate and other inorganic or mineral powders, chemical fertilizers such as ammonium sulfate, ammonium phosphate, ammonium nitrate, urea, ammonium chloride and the like, and compost. These carriers may be used either alone or as a mixture of two or more carriers.

The liquid carrier is that which itself has a solubility or which is without such solubility but is capable of dispersing an active ingredient with the aid of an adjuvant. The following are typical examples of the liquid carrier and can be used alone or as a mixture thereof. Water; alcohols such as methanol, ethanol, isopropanol, butanol and ethylene glycol; ketones such as acetone, methyl ethyl ketone, methyl isobutyl ketone, diisobutyl ketone and cyclohexanone; ethers such as ethyl ether, dioxane, cellosolve, dipropyl ether and tetrahydrofuran; aliphatic hydrocarbons such as kerosene and mineral oil; aromatic hydrocarbons such as benzene, toluene, xylene, solvent naphtha and alkylnaphthalene; halogenated hydrocarbons such as dichlorethane, chloroform, carbon tetrachloride and chlorobenzene; esters such as ethyl acetate, diisopropyl phthalate, dibutyl phthalate and dioctyl phthalate; amides such as dimethylformamide, diethylformamide and dimethylacetamide; nitrites such as acetonitrile; and dimethyl sulfoxide.

The following are typical examples of the adjuvant, which are used depending upon purposes and used alone or in combination of two or more adjuvants in some cases, or need not to be used at all.

To emulsify, disperse, dissolve and/or wet an active ingredient, a surfactant is used. As the surfactant, there can be exemplified polyoxyethylene alkyl ethers, polyoxyethylene alkylaryl ethers, polyoxyethylene higher fatty acid esters, polyoxyethylene resinates, polyoxyethylene sorbitan monolaurate, polyoxyethylene sorbitan monooleate, alkylarylsulfonates, naphthalene-sulfonic acid condensation products, ligninsulfonates and higher alcohol sulfate esters.

Further, to stabilize the dispersion of an active ingredient, tackify it and/or bind it, there may be used adjuvants such as casein, gelatin, starch, methyl cellulose, carboxymethyl cellulose, gum arabic, polyvinyl alcohols, turpentine, bran oil, bentonite and ligninsulfonates.

To improve the flowability of a solid product, there may be used adjuvants such as waxes, stearates and alkyl phosphates.

Adjuvants such as naphthalenesulfonic acid condensation products and polycondensates of phosphates may be used as a peptizer for dispersible products.

Adjuvants such as silicone oil may also be used as a defoaming agent.

The content of the active ingredient may be varied according to the need. In dusts or granules, the suitable content thereof is from 0.01 to 50% by weight. In emulsifiable concentrate and flowable wettable powder, too, the suitable content is from 0.01 to 50% by weight.

The agricultural and horticultural insecticide of the present invention is used to control a variety of insect pests in the following manner. That is, it is applied to a crop on which the insect pests are expected to appear or a site where appearance of the insect pests is undesirable, as it is or after being properly diluted with or suspended in water or the like, in an amount effective for control of the insect pests.

The applying dosage of the agrihorticultural insecticide of the present invention is varied depending upon various factors such as a purpose, insect pests to be controlled, a growth state of a plant, tendency of insect pests appearance, weather, environmental conditions, a preparation form, an application method, an application site and an application time. It may be properly chosen in a range of 0.1 g to 10 kg (in terms of active ingredient compound) per 10 are depending upon purposes.

The agricultural and horticultural insecticide of the present invention may be used in admixture with other agricultural and horticultural disease or pest controllers in order to expand both spectrum of controllable diseases and insect pest species and the period of time when effective applications are possible or to reduce the dosage.

Typical examples of the present invention are described below, but they should not be construed as limiting the scope of the invention.

EXAMPLE 1

Preparation of 3-Iodo-2-(4,4-dimethyloxazolin-2-yl)-2'-methyl-4'-heptafluoroisopropylbenzanilide (Compound No. 1-82)

823 Milligrams (1.44 mmols) of 3-iodo-$N^1$-(2-methyl-4-heptafluoroisopropylphenyl)-$N^2$-(2-hydroxy-1,1-dimethylethyl)phthalic acid diamide was dissolved in pyridine, and 200 mg (1.75 mmols) of methanesulfonyl chloride was added thereto, then the mixture was stirred at room temperature for 8 hours. The reaction mixture was concentrated under reduced pressure, the residue was diluted with ethyl acetate, then washed with water. The organic layer was dried over anhydrous sodium sulfate and concentrated under reduced pressure. The residue was purified by the silica gel column chromatography (hexane-ethyl acetate=2:1) to obtain 400 mg (yield: 50%) of the objective compound as white crystals.

EXAMPLE 2

Preparation of 3-chloro-2-(4,4-dimethylthiazolin-2-yl)-2'-methyl-4'-heptafluoroisopropylbenzanilide (Compound No. 1-85)

600 Milligrams (1.13 mmols) of 3-chloro-$N^1$-(2-methyl-4-heptafluoroisopropylphenyl)-$N^2$-(2-hydroxy-1,1-dimethylethyl)phthalic acid diamide was dissolved in toluene, and 500 mg (2.2 mmols) of diphosphorus pentasulfide was added thereto, then the mixture was stirred at 60° C. for 2 hours. After the reaction mixture was allowed to stand for cooling, 30% sodium hydroxide aqueous solution was added thereto and stirred for 30 minutes, after extraction the organic layer was washed with diluted hydrochloric acid and water. The organic layer was dried over anhydrous sodium sulfate, concentrated under reduced pressure, the residue was purified by the silica gel column chromatography (hexane-ethyl aceate=2:1) to obtain 23 mg (yield: 4%) the objective compound as white crystals.

EXAMPLE 3

Preparation of 2-chloro-6-(oxazol-2-yl)-2'-methyl-4'-heptafluoroisopropylbenzanilide (Compound No. 3-1)

200 Milligram (0.41 mmols) of 2-chloro-6-(oxazolin-2-yl)-2'-methyl-4'-heptafluoroisopropylbenzanilide was dissolved in fluorobenzene, and in the presence of 1 g of nickel oxide, the mixture was heated and refluxed for 8 hours. After the reaction mixture was allowed to stand for cooling, the catalyst was removed by filtration, the filtrate was concentrated under reduced pressure. The residue thus obtained was purified by the silica gel column chromatography (hexan-ethyl acetate=1:1) to obtain 61 mg (yield: 31%) of the objective compound as white crystals.

EXAMPLE 4

Preparation of 2-(2-t-butyloxazol-4-yl)-3-chloro-2'-methyl-4'-trifluoromethoxybenzanilide (Compound No. 4-1)

0.4 Gram of 2-(2-t-butyloxazol-4-yl)-3-chlorobenzoic acid was dissolved in 30 ml of tetrahydrofuran, then 0.3 g of 2-methyl-4-trifluoromethoxyaniline, 0.4 g of DEPC and 0.3 g of triethylamine were added thereto, the resulting mixture was heated under reflux for 3 hours with stirring. After completion of the reaction, the reaction mixture was poured into water, and the objective product was extracted with ethyl acetate, the organic layer was dried over anhydrous sodium sulfate, the residue obtained by removal of the solvent by distillation under reduced pressure was purified by the silica gel column chromatography to obtain 0.18 g (yield: 28%) of the objective product.

EXAMPLE 5

Preparation of 2-(5-t-butyloxadiazol-3-yl)-3-chloro-2'-methyl-4'-trifluoromethoxybenzanilide (Compound No. 5-3)

0.5 Gram of 2-(5-t-butyloxadiazol-3-yl)-3-chlorobenzoyl chloride was dissolved in 30 ml of tetrahydrofuran, and 0.3 g of 2-methyl-4-trifluoromethoxyaniline and 0.2 g of triethylamine were added thereto, the reaction was carried out for 1 hour under stirring. After completion of the reaction, the reaction mixture was poured into water, after extraction of the objective product with ethyl acetate, the organic layer was dried over anhydrous sodium sulfate, the solvent was removed by distillation under reduced pressure, the residue thus obtained was purified by a silica gel column chromatography to obtain 0.22 g (yield: 29%) of the objective product.

Typical preparation examples and test examples of the present invention are shown as follows. However, the scope of the present invention is not limited by these examples.

In the following formulation of examples, the "parts" means parts by weight.

Formulation Example 1

| | |
|---|---|
| Each compound listed in Tables 1 to 4 | 50 parts |
| Xylene | 40 parts |
| Mixture of polyoxyethylene nonylphenyl ether and calcium alkylbenzenesulfonate | 10 parts |

An emulsifiable concentrate was prepared by mixing uniformly the above ingredients to effect dissolution.

Formulation Example 2

| | |
|---|---|
| Each compound listed in Tables 1 to 4 | 3 parts |
| Clay powder | 82 parts |
| Diatomaceous earth powder | 15 parts |

A dust was prepared by mixing uniformly and grinding the above ingredients.

Formulation Example 3

| | |
|---|---|
| Each compound listed in Tables 1 to 4 | 5 parts |
| Mixed powder of bentonite and clay | 90 parts |
| Calcium ligninsulfonate | 5 parts |

Granules were prepared by mixing the above ingredients uniformly, and kneading the resulting mixture together with a suitable amount of water, followed by granulation and drying.

Formulation Example 4

| | |
|---|---|
| Each compound listed in Tables 1 to 4 | 20 parts |
| Mixture of kaolin and synthetic high-dispersion silicic acid | 75 parts |
| Mixture of polyoxyethylene nonylphenyl ether and calcium alkylbenzenesulfonate | 5 parts |

A wettable powder was prepared by mixing uniformly and grinding the above ingredients.

Test Example 1

Insecticidal Effect on Diamond Back Moth (*Plutella xylostella*)

Adult diamond back moths were released and allowed to oviposit on a Chinese cabbage seedling. Two days after the release, the seedling having the eggs deposited thereon was immersed for about 30 seconds in a liquid chemical prepared by diluting a preparation containing each compound listed in Tables 1 to 4 as an active ingredient to adjust the concentration to 500 ppm. After air-dryness, it was allowed to stand in a room thermostatted at 25° C. Six days after the immersion, the hatched insects were counted. The mortality was calculated according to the following equation and the insecticidal effect was judged according to the criterion shown below. The test was carried out with triplicate groups of 10 insects.

Corrected mortality (%) =

$$\frac{\text{Number of hatched insects in untreated group} - \text{Number of hatched insects in treated group}}{\text{Number of hatched insects in untreated group}} \times 100$$

Criterion
A—Mortality 100%
B—Mortality 99–90%
C—Mortality 89–80%
D—Mortality 79–50%

In the test mentioned above, the compounds which exhibited an activity ranking A or higher against diamond back moth (*Plutella xylostella*) were as follows:

1-6, 1-7, 1-8, 1-10, 1-13, 1-14, 1-15, 1-16, 1-17, 1-18, 1-19, 1-21, 1-22, 1-57, 1-65, 1-73, 1-82, 1-86, 1-90, 1-91, 1-92, 3-1, 3-2, 4-1, 5-1, 5-2 and 9-2.

Test Example 2
Insecticidal Effect on Common Cutworm (*Spodoptera litura*)

A piece of cabbage leaf (cultivar; Shikidori) was immersed for about 30 seconds in a liquid chemical prepared by diluting a preparation containing each compound listed in Tables 1 to 4 as an active ingredient to adjust the concentration to 500 ppm. After air-dryness, it was placed in a plastic Petri dish with a diameter of 9 cm and inoculated with second-instar larvae of common cutworm, after which the dish was closed and then allowed to stand in a room thermostatted at 25° C. Eight days after the inoculation, the dead and alive were counted. The mortality was calculated according to the following equation and the insecticidal effect was judged according to the criterion shown in Test Example 1. The test was carried out with triplicate groups of 10 insects.

Corrected mortality (%) =

$$\frac{\text{Number of alive larvae in untreated group} - \text{Number of alive larvae in treated group}}{\text{Number of alive larvae in untreated group}} \times 100$$

In the test mentioned above, the compounds which exhibited an activity ranking A or higher against Common cutworm (*Spodoptera litura*) were as follows:

1-13, 1-14, 1-16, 1-17, 1-20, 1-21, 1-22, 1-23, 1-57, 1-73, 1-82, 1-85, 1-86, 1-90, 1-92 and 9-2.

Test Example 3
Insecticidal Effect on Smaller Tea Tortrix (Adxophyes sp.)

Tea leaves were immersed for about 30 seconds in a liquid chemical prepared by diluting a preparation containing each compound listed in Tables 1 to 4 as an active ingredient to adjust the concentration to 500 ppm. After air-dryness, the tea leaves were placed in a plastic Petri dish with a diameter of 9 cm and inoculated with larvae of smaller tea tortrix, after which the dish was allowed to stand in a room thermostatted at 25° C. and having a humidity of 70%. Eight days after the inoculation, the dead and alive were counted and the insecticidal effect was judged according to the criterion shown in Test Example 1. The test was carried out with triplicate groups of 10 insects.

In the test mentioned above, the compounds which exhibited an activity ranking A or higher against smaller tea tortrix (Adxophyes sp.) were as follows:

1-1, 1-2, 1-6, 1-10, 1-13, 1-14, 1-15, 1-16, 1-17, 1-20, 1-21, 1-22, 1-23, 1-57, 1-65, 1-73, 1-82, 1-85, 1-86, 1-90, 1-91, 1-92, 3-2 and 9-2.

As described above, the agricultural and horticultural insecticide containing the benzamide derivative represented by the formula (I) of the present invention as an active ingredient have an excellent controlling effect against injurious insect pests, such as various agrohorticultural insect pests or grain strage pests doing harm on paddy rice, fruit trees, vegetables, crops, flower, ornamental plants and the like; sanitary insect pests; and nematodes and the like.

What is claimed is:

1. Benzamide derivatives represented by the general formula (I):

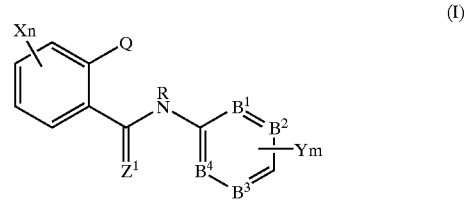

{wherein $Z^1$ is an oxygen atom or a sulfur atom; R is a hydrogen atom, an unsubstituted $C_1$–$C_6$ alkyl group, a substituted $C_1$–$C_6$ alkyl group having one or more substituents which may be the same or different and are selected from the group consisting of a halogen atom, a $C_1$–$C_6$ alkoxyl group, a $C_1$–$C_6$ alkylthio group, a $C_1$–$C_6$ alkylamino group and a di-$C_1$–$C_6$ alkylamino group whose $C_1$–$C_6$ alkyl groups may be the same or different, or a $C_1$–$C_6$ alkoxycarbonyl group;

X, which may be the same or different, are halogen atoms, cyano groups, nitro groups, $C_3$–$C_6$ cycloalkyl groups, halo-$C_3$–$C_6$ cycloalkyl groups, tri-$C_1$–$C_6$ alkylsilyl groups whose $C_1$–$C_6$ alkyl groups may be the same or different, unsubstituted phenyl groups, substituted phenyl groups having one or more substituents which may be the same or different and are selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and halo-$C_1$–$C_6$ alkylsulfonyl group, unsubstituted heterocyclic groups, substituted heterocyclic groups having one or more substitutents which may be the same or different and are selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group, or —$A^1$—$R^1$ [wherein $A^1$ is —O—, —S—, —SO—, —$SO_2$—, —C(=O)—, —C(=NOR$^2$)— (wherein $R^2$ is a hydrogen atom, $C_1$–$C_6$ alkyl group, a halo-$C_1$–$C_6$ alkyl group, a $C_3$–$C_6$ alkenyl group, a halo-$C_3$–$C_6$ alkenyl group, a $C_3$–$C_6$ alkynyl group, a $C_3$–$C_6$ cycloalkyl group, an unsubstituted phenyl-$C_1$–$C_4$ alkyl group, or a substituted phenyl-$C_1$–$C_4$ alkyl group having one or more substitutents which may be the same or different and are selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group), a $C_1$–$C_6$ alkylene group, a halo-$C_1$–$C_6$ alkylene group, a $C_2$–$C_6$ alkenylene group, a halo-$C_2$–$C_6$ alkenylene group, a $C_2$–$C_6$ alkynylene group and a halo $C_3$–$C_6$ alkynylene group, and $R^1$ is as follows:

(1) when $A^1$ is —O—, —S—, —SO— or —$SO_2$—, then $R^1$ is a halo-$C_3$–$C_6$ cycloalkyl group, a halo-$C_3$–$C_6$ cycloalkenyl group, an unsubstituted phenyl group, a substituted phenyl group having one or more substituents which may be the same or different and are selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group, an unsubstituted heterocyclic group, a substituted heterocyclic group having one or more substituents which may be the same or different and are selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group, or —$A^2$—$R^3$ (wherein $A^2$ is a $C_1$–$C_6$ alkylene group, a halo-$C_1$–$C_6$ alkylene group, a $C_3$–$C_6$ alkenylene group, a halo-$C_3$–$C_6$ alkenylene group, a $C_3$–$C_6$ alkynylene group or a halo-$C_3$–$C_6$ alkynylene group; $R^3$ is a hydrogen atom, a halogen atom, a $C_3$–$C_6$ cycloalkyl group, a halo-$C_3$–$C_6$ cycloalkyl group, a $C_1$–$C_6$ alkoxycarbonyl group, an unsubstituted phenyl group, a substituted phenyl group having one or more substituents which may be the same or different and are selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group, or —$A^3$—$R^4$ (wherein $A^3$ is —O—, —S—, —SO—, —$SO_2$— or —C(=O)—; $R^4$ is a $C_1$–$C_6$ alkyl group, a halo-$C_1$–$C_6$ alkyl group, a $C_3$–$C_6$ alkenyl group, a halo-$C_3$–$C_6$ alkenyl group, a $C_3$–$C_6$ cycloalkyl group, a halo-$C_3$–$C_6$ cycloalkyl group, an unsubstituted phenyl group, a substituted phenyl group having one or more substituents which may be the same or different and are selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group, an unsubstituted heterocyclic group, or a substituted heterocyclic group having one or more substituents which may be the same or different and are selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group));

(2) when $A^1$ is —C(=O)— or —C(=$NOR^2$)— (wherein $R^2$ is the same as defined above), then $R^1$ is a hydrogen atom, a $C_1$–$C_6$ alkyl group, a halo-$C_1$–$C_6$ alkyl group, a $C_2$–$C_6$ alkenyl group, a halo-$C_2$–$C_6$ alkenyl group, a $C_3$–$C_6$ cycloalkyl group, a halo-$C_3$–$C_6$ cycloalkyl group, a $C_1$–$C_6$ alkoxy group, a $C_1$–$C_6$ alkylthio group, a mono-$C_1$–$C_6$ alkylamino group, a di-$C_1$–$C_6$ alkylamino group whose $C_1$–$C_6$ alkyl groups may be the same or different, an unsubstituted phenyl group, a substituted phenyl group having one or more substituents which may be the same or different and are selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group, an unsubstituted phenylamino group, a substituted phenylamino group having one or more substituents which may be same or different and are selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group, an unsubstituted heterocyclic group, or a substituted heterocyclic group having one or more substituents which may be the same or different and are selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group;

(3) when $A^1$ is a $C_1$–$C_6$ alkylene group, a halo-$C_1$–$C_6$ alkylene group, a $C_2$–$C_6$ alkenylene group, a halo-$C_2$–$C_6$ alkenylene group, a $C_2$–$C_6$ alkynylene group or a halo-$C_3$–$C_6$ alkynylene group, then $R^1$ is a hydrogen atom, a halogen atom, a $C_3$–$C_6$ cycloalkyl group, a halo-$C_3$–$C_6$ cycloalkyl group, a $C_1$–$C_6$ alkoxycarbonyl group, a tri-$C_1$–$C_6$ alkylsilyl group whose $C_1$–$C_6$ alkyl groups may be the same or different, an unsubstituted phenyl group, a substituted phenyl group having one or more substituents which may be the same or different and are selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group, an unsubstituted heterocyclic group, a substituted heterocyclic group having one or more substituents which may be the same or different and are selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group, or —$A^4$—$R^5$ (wherein $A^4$ is —O—, —S—, —SO— or —$SO_2$—; $R^5$ is a $C_3$–$C_6$ cycloalkyl group, a halo-$C_3$–$C_6$ cycloalkyl group, an unsubstituted phenyl group, a substituted phenyl group having one or more substituents which may be the same or different and are selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group, an unsubstituted heterocyclic group, a substituted heterocyclic group having one or more substituents which may be the same or different and are selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group, or —$A^5$—$R^6$ (wherein $A^5$ is a $C_1$–$C_6$ alkylene group, a halo-$C_1$–$C_6$ alkylene group, a $C_2$–$C_6$ alkenylene group, a halo-$C_2$–$C_6$ alkenylene group, a $C_2$–$C_6$ alkynylene group, or a halo-$C_3$–$C_6$ alkynylene group; $R^6$ is a hydrogen atom, a halogen atom, a $C_3$–$C_6$ cycloalkyl group, a halo-$C_3$–$C_6$ cycloalkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group, an unsubstituted phenyl group, a substituted phenyl group having one or more substituents which may be the same or different and are selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group, an unsubstituted phenoxy group, a substituted phenoxy group having one or more substituents which may be the same or different and are selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group, an unsubstituted phenylthio group, a substituted phenylthio group having one or more substituents which may be the same or different and are selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group, an unsubstituted heterocyclic group, or a substituted heterocyclic group having one or more substituents which may be the same or different and are selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group))];

n is an integer of 0 to 4; further

X may be taken together with carbon atoms adjacent thereto on the phenyl ring to form a condensed ring, and said condensed ring may have one or more substituents which may be the same or different and are selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, an unsubstituted phenyl group, a substituted phenyl group having one or more substituents which may be the same or different and are selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group, an unsubstituted heterocyclic group, and a substituted heterocyclic group having one or more substituents which may be the same or different and are selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group;

$B^1$, $B^2$, $B^3$ and $B^4$ are carbon atoms; Y, which may be the same or different, are halogen atoms, cyano groups, nitro groups, halo-$C_3$–$C_6$ cycloalkyl groups, unsubstituted phenyl groups, substituted phenyl groups having one or more substituents which may be the same or different and are selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group, unsubstituted heterocyclic groups, substituted heterocyclic groups having one or more substituents which may be same or different and are selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group, or —$A^1$—$R^1$ (wherein $A^1$ and $R^1$ are the same as defined above);

m is an integer of 1 to 5; further

Y may be taken together with carbon atoms adjacent thereto on the aromatic ring to form a condensed ring, and said condensed ring may have one or more substituents which may be the same or different and are selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, an unsubstituted phenyl group, a substituted phenyl group having one or more substituents which may be the same or different and are selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group, an unsubstituted heterocyclic group, and a substituted heterocyclic group having one or more substituents which may be the same or different and are selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group;

Q is a heterocyclic group represented by each one of the following $Q^1$, $Q^3$ or $Q^4$:

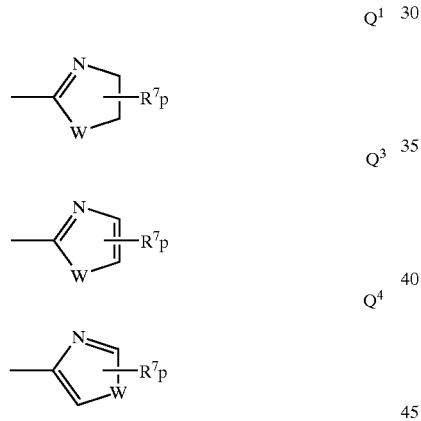

(wherein W is an oxygen atom, a sulfur atom or —(NR$^8$)— (wherein R$^8$ is a $C_1$–$C_6$ alkyl group, a halo-$C_1$–$C_6$ alkyl group, a $C_1$–$C_6$ alkoxy-$C_1$–$C_6$ alkyl group, a halo-$C_1$–$C_6$ alkoxy-$C_1$–$C_6$ alkyl group, a $C_1$–$C_6$ alkylthio-$C_1$–$C_6$ alkyl group, a halo-$C_1$–$C_6$ alkylthio-$C_1$–$C_6$ alkyl group, a $C_1$–$C_6$ alkylsulfinyl-$C_1$–$C_6$ alkyl group, a halo-$C_1$–$C_6$ alkylsulfinyl-$C_1$–$C_6$ alkyl group, a $C_1$–$C_6$ alkylsulfonyl-$C_1$–$C_6$ alkyl group, a halo-$C_1$–$C_6$ alkylsulfonyl-$C_1$–$C_6$ alkyl group, an unsubstituted phenyl group, a substituted phenyl group having one or more substituents which may be the same or different and are selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group, a $C_1$–$C_6$ alkylcarbonyl group, a halo-$C_1$–$C_6$ alkylcarbonyl group, a $C_1$–$C_6$ alkoxycarbonyl group, a $C_1$–$C_6$ alkylaminocarbonyl group, di-$C_1$–$C_6$ alkylaminocarbonyl group whose $C_1$–$C_6$ alkyl groups may be the same or different, an unsubstituted phenylcarbonyl group, a substituted phenylcarbonyl group having one or more substituents which may be the same or different and are selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group, an unsubstituted phenyl-$C_1$–$C_4$ alkoxycarbonyl group, or a substituted phenyl-$C_1$–$C_4$ alkoxycarbonyl group having one or more substituents which may be the same or different and are selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group);

R$^7$ is —(A$^6$)r—G$_l$ (wherein A$^6$ is a $C_1$–$C_8$ alkylene group, a $C_3$–$C_6$ alkenylene group or $C_3$–$C_6$ alkynylene group; r is an integer of 0 or 1; G, which may be the same or different, are hydrogen atoms, halogen atoms, cyano groups, nitro groups, halo-$C_1$–$C_6$ alkyl groups, $C_3$–$C_6$ cycloalkyl groups, halo-$C_3$–$C_6$ cycloalkyl groups, $C_1$–$C_6$ alkoxycarbonyl groups, di-$C_1$–$C_6$ alkoxyphosphoryl groups whose $C_1$–$C_6$ alkoxy groups may be the same or different, di-$C_1$–$C_6$ alkoxythiophosphoryl groups whose $C_1$–$C_6$ alkoxy groups may be the same or different, diphenylphosphino groups, diphenylphosphono groups, unsubstituted phenyl groups, substituted phenyl groups having one or more substituents which may be the same or different and are selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group, unsubstituted biphenyl groups, substituted biphenyl groups having one or more substituents which may be the same or different and are selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group, unsubstituted heterocyclic groups, substituted heterocyclic groups having one or more substituents which may be the same or different and are selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group, or —A$^7$—R$^9$ [wherein A$^7$ is —O—, —S—, —SO—, —SO$_2$—, —N(R$^{10}$)— (wherein R$^{10}$ is a hydrogen atom, a $C_1$–$C_6$ alkylcarbonyl group, a halo-$C_1$–$C_6$ alkylcarbonyl group, a $C_1$–$C_6$ alkoxycarbonyl group, a $C_1$–$C_6$ alkylaminocarbonyl group, a di-$C_1$–$C_6$ alkylaminocarbonyl group whose $C_1$–$C_6$ alkyl groups may be the same or different, an unsubstituted phenylcarbonyl group, a substituted phenylcarbonyl group having one or more substituents which may be the same or different and are selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group, an unsubstituted phenyl-$C_1$–$C_4$ alkoxycarbonyl group, a substituted phenyl-$C_1$–$C_4$ alkoxycarbonyl group having one or more substituents which may be the same or different and are selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group, a $C_1$–$C_6$ alkylsulfonyl group or a halo-$C_1$–$C_6$ alkylsulfonyl group), —C(=O)— or —C(=NOR$^2$)—, (wherein R$^2$ is the same as defined above) and R$^9$ is as follows:

(1) when A$^7$ is —O—, —S— or —N(R$^{10}$)— (wherein R$^{10}$ is the same as defined above), then R$^9$ is a hydrogen atom, a $C_1$–$C_6$ alkyl group, a halo-$C_1$–$C_6$ alkyl group, a $C_3$–$C_6$ alkenyl group, a halo-$C_3$–$C_6$ alkenyl group, a $C_3$–$C_6$ alkynyl group, a halo-$C_3$–$C_6$ alkynyl group, a $C_3$–$C_6$ cycloalkyl group, a halo-$C_3$–$C_6$ cycloalkyl group, a $C_1$–$C_6$ alkylcarbonyl group, a halo-$C_1$–$C_6$ alkylcarbonyl group, a $C_1$–$C_6$ alkoxycarbonyl group, an unsubstituted phenyl group, a substituted phenyl group having one or more substituents which may be the same or different and are selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group, an unsubstituted phenyl-$C_1$–$C_4$ alkyl group, a substituted phenyl-$C_1$–$C_4$ alkyl group having one or more substituents in the phenyl ring which may be the same or different and are selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group, an unsubstituted heterocyclic group, or a substituted heterocyclic group having one or more substituents which may be the same or different and are selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group;

(2) when A$^7$ is —SO—, —SO$_2$—, —C(=O)— or —C(=NOR$^2$)— (wherein R$^2$ is the same as defined above), then R$^9$ is a hydrogen atom, a $C_1$–$C_6$ alkyl group, a halo-$C_1$–$C_6$ alkyl group, a $C_3$–$C_6$ alkenyl group, a halo-$C_3$–$C_6$ alkenyl group, a $C_3$–$C_6$ cycloalkyl group, a halo-$C_3$–$C_6$ cycloalkyl group, a $C_1$–$C_6$ alkoxy group, a $C_1$–$C_6$ alkylthio group, a mono-$C_1$–$C_6$ alkylamino group, a di-$C_1$–$C_6$ alkylamino group whose $C_1$–$C_6$ alkyl groups may be the same or different, an unsubstituted phenyl group, a substituted phenyl group having one or more substituents which may be the same or different and are selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group, an unsubstituted phenylamino group, a substituted phenylamino group having one or more substituents which may be the same or different in the phenyl ring and are selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group, an unsubstituted heterocyclic group, or a substituted heterocyclic group having one or more substituents which may be the same or different and are selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group];

l is an integer of 1 to 4); and p is as follows, (1) when Q is Q$^1$, then p is an integer of 1–4; and R$^7$ may form 5–7 membered heterocyclic group by bonding together with carbon atoms adjacent thereto on the heterocyclic group, and the newly formed 5–7 membered heterocyclic group may be interrupted by 1–3 heteroatoms which may be the same or different and selected from oxygen atom, sulfur atom and nitrogen atom, additionally, R$^7$ may form 3–7 membered heterocyclic group by bonding together with the same carbon atoms being bonded thereto on the heterocyclic group, and the newly formed 3–7 membered heterocyclic group may be interrupted by 1–3 heteroatoms which may be the same or different and selected from oxygen atom, sulfur atom and nitrogen atom;

(2) when Q is Q$^3$, then p is an integer of 1–2; and R$^7$ may form 5–7 membered heterocyclic group by bonding together with carbon atoms adjacent thereto on the heterocyclic group, and the newly formed 5–7 membered heterocyclic group may be interrupted by 1–3 heteroatoms which may be the same or different and selected from oxygen atom, sulfur atom and nitrogen atom;

(3) when Q is Q$^4$, then p is an integer of 1–2)}.

2. The benzamide derivatives according to claim 1, wherein Z$^1$ is an oxygen atom; R is a hydrogen atom or a $C_1$–$C_6$ alkyl group; X, which may be the same or different, are halogen atoms, nitro groups, halo-$C_1$–$C_6$ alkyl groups, halo-$C_1$–$C_6$ alkoxy groups, or halo-$C_1$–$C_6$ alkylthio groups; n is an integer of 0 to 4; $B^1$, $B^2$, $B^3$ and $B^4$ are carbon atoms; Y, which may be the same or different, are halogen atoms, $C_1$–$C_6$ alkyl groups, halo-$C_1$–$C_6$ alkyl groups, $C_1$–$C_6$ alkoxy groups, halo-$C_1$–$C_6$ alkoxy groups, $C_1$–$C_6$ alkylthio groups, halo-$C_1$–$C_6$ alkylthio groups, halo-$C_1$–$C_6$ alkoxyhalo-$C_1$–$C_6$ alkyl groups, halo-$C_1$–$C_6$ alkoxyhalo-$C_1$–$C_6$ alkoxy groups, halo-$C_1$–$C_6$ alkoxyhalo-$C_1$–$C_6$ alkylthio groups, halo-$C_1$–$C_6$ alkylsulfinyl groups, halo-$C_1$–$C_6$ alkylsulfonyl groups, substituted phenyl groups having one or more substituents which may be the same or different and are selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group, substituted phenoxy groups having one or more of substituents which may be the same or different and are selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group, or substituted pyridyloxy groups having one or more substituents which may be the same or different and are selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group; m is an integer of 1 to 5; further, Y may be taken together with the carbon atoms adjacent thereto on the aromatic ring to form a condensed ring, and said condensed ring may have one or more substituents which may be the same or different and are selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group;

Q is a heterocyclic group represented by the following $Q^1$, $Q^3$ or $Q^4$ or; (wherein W is an oxygen atom, a sulfur atom or —N($R^8$)— (wherein $R^8$ is a $C_1$–$C_6$ alkyl

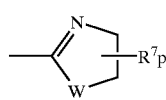

$Q^1$

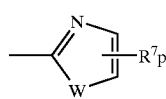

$Q^3$

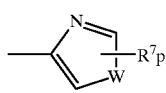

$Q^4$ group, a $C_1$–$C_6$ alkylcarbonyl group, a $C_1$–$C_6$ alkoxycarbonyl group, a $C_1$–$C_6$ alkylaminocarbonyl group, or di-$C_1$–$C_6$ alkylaminocarbonyl group whose $C_1$–$C_6$ alkyl groups may be the same or different);

$R^7$ is —($A^6$)r—$G_l$ (wherein $A^6$ is a $C_1$–$C_8$ alkylene group;

r is an integer of 0 or 1;

G, which may be the same or different, are hydrogen atoms, halogen atoms, cyano groups, $C_3$–$C_6$ cycloalkyl groups, halo-$C_3$–$C_6$ cycloalkyl groups, $C_1$–$C_6$ alkoxycarbonyl groups, unsubstituted phenyl groups, substituted phenyl groups having one or more substituents which may be the same or different and are selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group, unsubstituted biphenyl groups, substituted biphenyl groups having one or more substituents which may be the same or different and are selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group, unsubstituted heterocyclic groups, substituted heterocyclic groups having one or more substituents which may be the same or different and are selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group, or —$A^7$—$R^9$ [wherein $A^7$ is —O—, —S—, —SO—, —$SO_2$—, —N($R^{10}$)— (wherein $R^{10}$ is a hydrogen atom, a $C_1$–$C_6$ alkylcarbonyl group, a halo-$C_1$–$C_6$ alkylcarbonyl group, a $C_1$–$C_6$ alkoxycarbonyl group, a $C_1$–$C_6$ alkylaminocarbonyl group, a di-$C_1$–$C_6$ alkylaminocarbonyl group whose $C_1$–$C_6$ alkyl groups may be the same or different, a $C_1$–$C_6$ alkylsulfonyl group or a halo-$C_1$–$C_6$ alkylsulfonyl group), —C(=O)— or —C(=NO$R^2$)— (wherein $R^2$ is a hydrogen atom, a $C_1$–$C_6$ alkyl group or a halo-$C_1$–$C_6$ alkyl group), and $R^9$ is as follows:

(1) when $A^7$ is —O—, —S— or —N($R^{10}$)— (wherein $R^{10}$ is the same as defined above), then $R^9$ is a $C_1$–$C_6$ alkyl group, a halo-$C_1$–$C_6$ alkyl group, a $C_3$–$C_6$ cycloalkyl group, a halo-$C_3$–$C_6$ cycloalkyl group, an unsubstituted phenyl group, a substituted phenyl group having one or more substituents which may be the same or different and are selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group, an unsubstituted phenyl-$C_1$–$C_4$ alkyl group, a substituted phenyl-$C_1$–$C_4$ alkyl group having one or more substituents in the phenyl ring which may be the same or different and are selected from the group consisting of a halogen atom, a $C_1-C_6$ alkyl group, a halo-$C_1-C_6$ alkyl group, a $C_1-C_6$ alkoxy group, a halo-$C_1-C_6$ alkoxy group, a $C_1-C_6$ alkylthio group, a halo-$C_1-C_6$ alkylthio group, a $C_1-C_6$ alkylsulfinyl group, a halo-$C_1-C_6$ alkylsulfinyl group, a $C_1-C_6$ alkylsulfonyl group and a halo-$C_1-C_6$ alkylsulfonyl group, an unsubstituted heterocyclic group, or a substituted heterocyclic group having one or more substituents which may be the same or different and are selected from the group consisting of a halogen atom, a $C_1-C_6$ alkyl group, a halo-$C_1-C_6$ alkyl group, a $C_1-C_6$ alkoxy group, a halo-$C_1-C_6$ alkoxy group, a $C_1-C_6$ alkylthio group, a halo-$C_1-C_6$ alkylthio group, a $C_1-C_6$ alkylsulfinyl group, a halo-$C_1-C_6$ alkylsulfinyl group, a $C_1-C_6$ alkylsulfonyl group and a halo-$C_1-C_6$ alkylsulfonyl group;

(2) when $A^7$ is —SO—, —SO$_2$—, —C(=O)— or —C(NOR$^2$)— (wherein $R^2$ is the same as defined above), then $R^9$ is a $C_1-C_6$ alkyl group, a halo-$C_1-C_6$ alkyl group, a $C_3-C_6$ cycloalkyl group, a halo-$C_3-C_6$ cycloalkyl group, a $C_1-C_6$ alkoxy group, a $C_1-C_6$ alkylthio group, a mono-$C_1-C_6$ alkylamino group, a di-$C_1-C_6$ alkylamino group whose $C_1-C_6$ alkyl groups may be the same or different, an unsubstituted phenyl group, a substituted phenyl group having one or more substituents which may be the same or different and are selected from the group consisting of a halogen atom, a $C_1-C_6$ alkyl group, a halo-$C_1-C_6$ alkyl group, a $C_1-C_6$ alkoxy group, a halo-$C_1-C_6$ alkoxy group, a $C_1-C_6$ alkylthio group, a halo-$C_1-C_6$ alkylthio group, a $C_1-C_6$ alkylsulfinyl group, a halo-$C_1-C_6$ alkylsulfinyl group, a $C_1-C_6$ alkylsulfonyl group and a halo-$C_1-C_6$ alkylsulfonyl group, an unsubstituted heterocyclic group, or a substituted heterocyclic group having one or more substituents which may be the same or different and are selected from the group consisting of a halogen atom, a $C_1-C_6$ alkyl group, a halo-$C_1-C_6$ alkyl group, a $C_1-C_6$ alkoxy group, a halo-$C_1-C_6$ alkoxy group, a $C_1-C_6$ alkylthio group, a halo-$C_1-C_6$ alkylthio group, a $C_1-C_6$ alkylsulfinyl group, a halo-$C_1-C_6$ alkylsulfinyl group, a $C_1-C_6$ alkylsulfonyl group and a halo-$C_1-C_6$ alkylsulfonyl group];

l is an integer of 1 to 4); and p is as follows, (1) when Q is $Q^1$, then p is an integer of 1–4; and $R^7$ may form 5–7 membered heterocyclic group by bonding together with carbon atoms adjacent thereto on the heterocyclic group, and the newly formed 5–7 membered heterocyclic group may be interrupted by 1–3 heteroatoms which may be the same or different and selected from oxygen atom, sulfur atom and nitrogen atom, additionally, $R^7$ may form 3–7 membered heterocyclic group by bonding together with the same carbon atoms being bonded thereto on the heterocyclic group, and the newly formed 3–7 membered heterocyclic group may be interrupted by 1–3 heteroatoms which may be the same or different and selected from oxygen atom, sulfur atom and nitrogen atom;

(2) when Q is $Q^3$, then p is an integer of 1–2; and $R^7$ may form 5–7 membered heterocyclic group by bonding together with carbon atoms adjacent thereto on the heterocyclic group, and the newly formed 5–7 membered heterocyclic group may be interrupted by 1–3 heteroatoms which may be the same or different and selected from oxygen atom, sulfur atom and nitrogen atom;

(3) when Q is $Q^4$, then p is an integer of 1–2).

3. A benzamide derivative according to claim 2, wherein Q is $Q^3$ or $Q^4$.

4. A benzamide derivative according to claim 2, wherein Q is $Q^1$ and W is an oxygen atom.

5. An agricultural and horticultural insecticide characterized by containing, as the effective ingredient, the benzamide derivative according to claim 1.

6. A method for applying the agricultural and horticultural insecticide, characterized by treating an objective crop or soil with an effective amount of an agricultural and horticultural insecticide according to claim 5 in order to protect useful crops against insect pests.

* * * * *